United States Patent
Schmitz et al.

(10) Patent No.: US 9,829,417 B2
(45) Date of Patent: Nov. 28, 2017

(54) ENVIRONMENTAL CONDITIONING ASSEMBLY FOR USE IN MECHANICAL TESTING AT MICRON OR NANO-SCALES

(71) Applicant: Hysitron, Inc., Eden Prairie, MN (US)

(72) Inventors: Roger William Schmitz, Hutchinson, MN (US); Ude D. Hangen, Aachen (DE); Lucas Paul Keranen, Hutchinson, MN (US); Ryan Major, Plymouth, MN (US); Yunje Oh, Medina, MN (US); Jeremiah Vieregge, Eden Prairie, MN (US); Christopher David Young, Excelsior, MN (US)

(73) Assignee: Hysitron, Inc., Eden Prairie, MN (US)

( * ) Notice: Subject to any disclaimer, the term of this patent is extended or adjusted under 35 U.S.C. 154(b) by 0 days.

(21) Appl. No.: 14/407,783

(22) PCT Filed: Mar. 14, 2013

(86) PCT No.: PCT/US2013/031650
§ 371 (c)(1),
(2) Date: Dec. 12, 2014

(87) PCT Pub. No.: WO2013/187972
PCT Pub. Date: Dec. 19, 2013

(65) Prior Publication Data
US 2015/0185117 A1    Jul. 2, 2015

Related U.S. Application Data

(60) Provisional application No. 61/659,391, filed on Jun. 13, 2012.

(51) Int. Cl.
*G01N 3/42*    (2006.01)
*G01N 1/28*    (2006.01)
(Continued)

(52) U.S. Cl.
CPC .............. *G01N 1/28* (2013.01); *F28F 9/26* (2013.01); *G01B 3/00* (2013.01); *G01N 1/44* (2013.01);
(Continued)

(58) Field of Classification Search
CPC ............ G01N 3/42; G01N 2203/0286; G01N 2203/0226; G01N 17/002;
(Continued)

(56) References Cited

U.S. PATENT DOCUMENTS 3,028,754 A    4/1962    Huyser
3,896,314 A    7/1975    Nukui et al.
(Continued)

FOREIGN PATENT DOCUMENTS

EP    0855452 A1    7/1998
EP    2011066018 A1    6/2011
(Continued)

OTHER PUBLICATIONS

"U.S. Appl. No. 13/510,825, Notice of Allowance mailed Jan. 29, 2016", 7 pgs.
(Continued)

*Primary Examiner* — David A Rogers
(74) *Attorney, Agent, or Firm* — Schwegman Lundberg & Woessner, P.A.

(57) ABSTRACT

An environmental conditioning assembly for use in mechanical testing at scales of microns or less. The assembly includes an enclosure housing with an environmental cavity therein. A sample stage is positioned within the environmental cavity and includes an option sample heater. The enclosure housing includes a cavity perimeter clustered around the sample stage, and the enclosure housing isolates the environmental cavity and the sample stage from an environment exterior to the enclosure housing. In an
(Continued)

example, an expansion and contraction linkage maintains a sample on the sample stage at a static elevation according to heating or cooling fluctuations within the environmental cavity. A testing instrument access port extends through the enclosure housing into the environmental cavity.

29 Claims, 7 Drawing Sheets

(51) Int. Cl.
    *G01B 3/00*         (2006.01)
    *F28F 9/26*         (2006.01)
    *G01N 1/44*         (2006.01)
    *G01N 19/00*       (2006.01)
    *G01N 27/14*       (2006.01)

(52) U.S. Cl.
    CPC .............. *G01N 19/00* (2013.01); *G01N 27/14* (2013.01); *G01N 3/42* (2013.01)

(58) Field of Classification Search
    CPC ... G01N 2203/0078; G01N 2203/0098; G01N 2203/0232; G01N 3/08
    See application file for complete search history.

(56) References Cited

U.S. PATENT DOCUMENTS

| | | | |
|---|---|---|---|
| 4,346,754 A * | 8/1982 | Imig ...................... | G01N 3/02 165/254 |
| 4,474,015 A * | 10/1984 | Christmas ................ | A01N 1/00 62/3.2 |
| 4,491,788 A | 1/1985 | Zandonatti | |
| 4,703,181 A | 10/1987 | Swann et al. | |
| 4,735,092 A * | 4/1988 | Kenny ...................... | G01N 3/18 73/840 |
| 4,820,051 A * | 4/1989 | Yanagisawa ............. | G01N 3/42 356/626 |
| 4,917,462 A | 4/1990 | Lewis et al. | |
| 4,992,660 A | 2/1991 | Kobayashi | |
| 4,996,433 A | 2/1991 | Jones et al. | |
| 5,015,825 A | 5/1991 | Brindley | |
| 5,202,542 A | 4/1993 | Ferguson | |
| 5,331,134 A | 7/1994 | Kimura | |
| 5,367,171 A | 11/1994 | Aoyama et al. | |
| 5,507,189 A * | 4/1996 | Kim ......................... | G01N 3/28 73/834 |
| 5,512,727 A | 4/1996 | Myers et al. | |
| 5,553,486 A * | 9/1996 | Bonin ..................... | B82Y 35/00 361/283.1 |
| 5,654,546 A | 8/1997 | Lindsay | |
| 5,661,235 A | 8/1997 | Bonin | |
| 5,731,587 A | 3/1998 | Dibattista et al. | |
| 5,821,545 A | 10/1998 | Lindsay et al. | |
| 5,869,751 A | 2/1999 | Bonin | |
| 6,026,677 A * | 2/2000 | Bonin ..................... | B82Y 35/00 361/283.2 |
| 6,339,958 B1 | 1/2002 | Tsui et al. | |
| 6,495,838 B1 | 12/2002 | Yaguchi et al. | |
| 6,520,004 B1 | 2/2003 | Lin | |
| 6,840,305 B2 * | 1/2005 | Zheng ..................... | G01N 11/14 165/11.1 |
| 7,274,450 B1 | 9/2007 | Green et al. | |
| 7,451,636 B2 | 11/2008 | Bradshaw et al. | |
| 7,674,037 B2 * | 3/2010 | Liu ........................... | G01K 1/14 374/137 |
| 7,685,868 B2 * | 3/2010 | Woirgard ................ | G01N 3/42 73/81 |
| 7,685,869 B2 * | 3/2010 | Bonilla ................... | B82Y 35/00 73/105 |
| 7,798,011 B2 * | 9/2010 | Warren ................... | B82Y 35/00 73/780 |
| 7,878,071 B2 * | 2/2011 | Greer ....................... | G01N 3/08 73/777 |
| 8,042,405 B2 * | 10/2011 | Shuaib ................... | B21D 22/20 73/799 |
| 8,065,929 B2 * | 11/2011 | Yakimoski ............... | G01N 3/08 73/865.6 |
| 8,161,803 B2 * | 4/2012 | Oh ........................... | G01N 3/42 73/105 |
| 8,434,370 B2 * | 5/2013 | Oh ......................... | B81C 99/005 73/774 |
| 8,474,324 B2 * | 7/2013 | Rihan ................... | G01N 17/006 73/799 |
| 8,479,589 B2 * | 7/2013 | Shuaib ................... | B21D 22/20 73/760 |
| 8,569,714 B2 | 10/2013 | Han et al. | |
| 8,631,687 B2 * | 1/2014 | Patten ..................... | G01N 3/42 73/81 |
| 8,844,368 B2 | 9/2014 | Peecock et al. | |
| 9,189,592 B2 * | 11/2015 | Nam .................... | G06F 17/5086 |
| 9,304,072 B2 | 4/2016 | Syed Asif et al. | |
| 9,316,569 B2 | 4/2016 | Oh et al. | |
| 9,759,641 B2 | 9/2017 | Oh et al. | |
| 2002/0110177 A1 | 8/2002 | Nakayama et al. | |
| 2003/0140684 A1 * | 7/2003 | Broz ....................... | G01N 3/48 73/81 |
| 2006/0025002 A1 | 2/2006 | Zhang et al. | |
| 2006/0180577 A1 | 8/2006 | Lindeman | |
| 2007/0180924 A1 | 8/2007 | Warren et al. | |
| 2007/0278420 A1 | 12/2007 | Molhave | |
| 2008/0092938 A1 | 4/2008 | Majumdar et al. | |
| 2008/0169428 A1 * | 7/2008 | Schoenlein .......... | G01N 17/002 250/453.11 |
| 2008/0266653 A1 * | 10/2008 | Korpinen ............... | G02B 21/26 359/368 |
| 2008/0276727 A1 | 11/2008 | Enoksson et al. | |
| 2008/0290290 A1 | 11/2008 | Nagakubo et al. | |
| 2009/0044609 A1 * | 2/2009 | Sawa ....................... | G01N 3/42 73/81 |
| 2009/0111701 A1 | 4/2009 | Ahn et al. | |
| 2009/0120172 A1 | 5/2009 | Bradshaw et al. | |
| 2009/0194689 A1 | 8/2009 | Abramson et al. | |
| 2009/0206258 A1 | 8/2009 | Kasai et al. | |
| 2009/0289050 A1 | 11/2009 | Ondricek | |
| 2010/0095780 A1 | 4/2010 | Oh et al. | |
| 2010/0107745 A1 * | 5/2010 | Bonin ...................... | G01N 3/42 73/105 |
| 2010/0132441 A1 | 6/2010 | Oh et al. | |
| 2010/0180356 A1 | 7/2010 | Bonilla et al. | |
| 2010/0186520 A1 | 7/2010 | Wheeler, IV et al. | |
| 2010/0212411 A1 | 8/2010 | Passilly et al. | |
| 2010/0294147 A1 | 11/2010 | Loiret-bernal et al. | |
| 2011/0107472 A1 | 5/2011 | Han et al. | |
| 2011/0152724 A1 | 6/2011 | Hansma et al. | |
| 2011/0252874 A1 | 10/2011 | Patten et al. | |
| 2012/0292528 A1 | 11/2012 | Oh et al. | |
| 2013/0098145 A1 * | 4/2013 | Oh ........................... | G01N 3/42 73/81 |
| 2014/0293293 A1 * | 10/2014 | Vodnick ................ | G01B 21/047 356/614 |
| 2014/0331782 A1 | 11/2014 | Keranen et al. | |
| 2015/0033835 A1 | 2/2015 | Asif et al. | |
| 2015/0179397 A1 | 6/2015 | Damiano, Jr. et al. | |
| 2016/0123859 A1 | 5/2016 | Oh et al. | |

FOREIGN PATENT DOCUMENTS

| | | |
|---|---|---|
| EP | 2861934 A | 4/2015 |
| EP | 2861934 B1 | 5/2017 |
| GB | 2116459 A | 9/1993 |
| JP | 4996867 A | 12/1972 |
| JP | 4996867 U | 8/1974 |
| JP | 55088256 A | 7/1980 |
| JP | 5691598 A | 7/1981 |
| JP | 57201953 A | 12/1982 |
| JP | 6327731 A | 3/1983 |
| JP | 58173159 A | 10/1983 |
| JP | 58173159 U | 11/1983 |

(56) References Cited

FOREIGN PATENT DOCUMENTS

| JP | 5915635 A | 1/1984 |
|---|---|---|
| JP | 60127540 A | 7/1985 |
| JP | 181553 U | 5/1989 |
| JP | 01081553 U | 5/1989 |
| JP | 01119153 A | 5/1989 |
| JP | 0366122 A | 3/1991 |
| JP | 04131741 A | 5/1992 |
| JP | 0566186 A | 3/1993 |
| JP | 0572457 A | 3/1993 |
| JP | 06315299 A | 11/1994 |
| JP | 2000241325 A | 9/2000 |
| JP | 2000241332 A | 9/2000 |
| JP | 2002116130 A | 4/2002 |
| JP | 2002318318 A | 10/2002 |
| JP | 2008512841 A | 4/2008 |
| JP | 2008134191 A | 6/2008 |
| JP | 2008197000 A | 8/2008 |
| JP | 2009526230 A | 7/2009 |
| JP | 2009193833 A | 8/2009 |
| JP | 2013512545 A | 4/2013 |
| JP | 2015501935 A | 1/2015 |
| JP | 6162770 | 6/2017 |
| WO | WO-2008061224 A1 | 5/2008 |
| WO | WO-2011066018 A1 | 6/2011 |
| WO | WO-2013074623 A1 | 5/2013 |
| WO | WO-2013082145 A1 | 6/2013 |
| WO | WO-2013082148 A1 | 6/2013 |
| WO | WO-2013187972 A1 | 12/2013 |

OTHER PUBLICATIONS

"U.S. Appl. No. 14/948,549, Preliminary Amendment filed Jan. 14, 2016", 9 pgs.
"European Application Serial No. 12853899.8, Response filed Jan. 26, 2016 to Extended European Search Report mailed Jun. 29, 2015", 12 pgs.
"U.S. Appl. No. 13/510,825, Final Office Action mailed Dec. 26, 2014", 17 pgs.
"U.S. Appl. No. 13/510,825, Response filed Mar. 25, 2015 to Final Office Action mailed Dec. 26, 2014", 22 pgs.
"International Application Serial No. PCT/US2013/031650, International Preliminary Report on Patentability mailed Dec. 24, 2014", 6 pgs.
"Japanese Application Serial No. [Pending], Amendment filed Jan. 30, 2015" with GIST English translation (translated Apr. 12, 2015), 55 pgs.
U.S. Appl. No. 14/948,549, filed Nov. 23, 2015, Micro Electro-Mechanical Heater.
"U.S. Appl. No. 13/090,036, Notice of Allowance mailed Mar. 19, 2013", 8 pgs.
"U.S. Appl. No. 13/090,036, Notice of Allowance mailed Jul. 15, 2013", 9 pgs.
"U.S. Appl. No. 13/510,825, Examiner Interview Summary mailed Jul. 10, 2013", 3 pgs.
"U.S. Appl. No. 13/510,825, Examiner Interview Summary mailed Nov. 18, 2014", 3 pgs.
"U.S. Appl. No. 13/510,825, Final Office Action mailed Aug. 27, 2013", 26 pgs.
"U.S. Appl. No. 13/510,825, Non Final Office Action mailed Mar. 27, 2013", 14 pgs.
"U.S. Appl. No. 13/510,825, Non Final Office Action mailed Jun. 3, 2014", 28 pgs.
"U.S. Appl. No. 13/510,825, Preliminary Amendment filed May 18, 2012", 3 pgs.
"U.S. Appl. No. 13/510,825, Response filed Jun. 27, 2013 to Non Final Office Action mailed Mar. 27, 2013", 30 pgs.
"U.S. Appl. No. 13/510,825, Response filed Nov. 19, 2014 to Non Final Office Action mailed Jun. 3, 2014", 20 pgs.
"U.S. Appl. No. 13/510,825, Response filed Nov. 26, 2013 to Final Office Action mailed Aug. 27, 2013", 34 pgs.

"U.S. Appl. No. 14/358,065, Preliminary Amendment filed May 14, 2014", 8 pgs.
"U.S. Appl. No. 14/361,094, Preliminary Amendment filed May 28, 2014", 8 pgs.
"U.S. Appl. No. 14/361,133, Preliminary Amendment filed May 28, 2014", 8 pgs.
"Application Serial No. PCT/US2012/065009, Article 19 Amendment filed Mar. 25, 2013", 6 pgs.
"European Application Serial No. 10833722.1, Preliminary Amendment filed Jan. 21, 2013", 21 pgs.
"International Application Serial No. PCT/US2010/046865, International Preliminary Report on Patentability mailed May 30, 2012", 10 pgs.
"International Application Serial No. PCT/US2010/046865, International Search Report mailed Oct. 28, 2010", 2 pgs.
"International Application Serial No. PCT/US2010/046865, Written Opinion mailed Oct. 28, 2010", 8 pgs.
"International Application Serial No. PCT/US2012/065009, Supplemental Article 19 Amendment filed Apr. 26, 2013", 12 pgs.
"International Application Serial No. PCT/US2012/065009, International Preliminary Report on Patentability mailed May 30, 2014", 7 pgs.
"International Application Serial No. PCT/US2012/065009, International Search Report mailed Jan. 25, 2013", 2 pgs.
"International Application Serial No. PCT/US2012/065009, Written Opinion mailed Jan. 25, 2013", 5 pgs.
"International Application Serial No. PCT/US2012/066842, Demand and Response filed Sep. 27, 2013 to Written Opinion mailed Feb. 7, 2013", 25 pgs.
"International Application Serial No. PCT/US2012/066842, International Preliminary Report on Patentability mailed Jun. 12, 2014", 10 pgs.
"International Application Serial No. PCT/US2012/066842, International Preliminary Report on Patentability mailed Dec. 6, 2013", 36 pgs.
"International Application Serial No. PCT/US2012/066842, International Search Report mailed Feb. 7, 2013", 2 pgs.
"International Application Serial No. PCT/US2012/066842, Written Opinion mailed Feb. 7, 2013", 8 pgs.
"International Application Serial No. PCT/US2012/066846, Demand and Response filed Sep. 27, 2013 to Written Opinion mailed Feb. 6, 2013", 26 pgs.
"International Application Serial No. PCT/US2012/066846, International Preliminary Report on Patentability mailed Dec. 3, 2013", 16 pgs.
"International Application Serial No. PCT/US2012/066846, International Search Report mailed Feb. 6, 2013", 2 pgs.
"International Application Serial No. PCT/US2012/066846, Written Opinion mailed Feb. 6, 2013", 8 pgs.
"International Application Serial No. PCT/US2013/031650, International Search Report mailed May 31, 2013", 2 pgs.
"International Application Serial No. PCT/US2013/031650, Written Opinion mailed May 31, 2013", 4 pgs.
"Japanese Application Serial No. 2012-541077, Office Action mailed Mar. 18, 2014", w/English translation, 4 pgs.
Allard, L. F., et al., "A New Paradigm for Ultra-High-Resolution Imaging at Elevated Temperatures", Microscopy and Microanalysis, 14(Supp. S2), (2008), 792-793.
Briceno, M., et al., "In-situ TEM Observations on the Sintering Process of Colloidal Gold Using an Ultra-fast Heating Stage", Microscopy and Microanalysis, 14(Suppl 2), (2008), 1336-1337.
Damiano, John, et al., "A MEMS-based Technology Platform for in-situ TEM Heating Studies", Microscopy and Microanalysis, 14(Suppl 2), (2008), 1332-1333.
Eakins, D. E., et al., "An in situ TEM study of phase formation in gold-aluminum couples", Journal of Materials Science, 39, (2004), 165-171.
Kamino, T., et al., "A newly developed high resolution hot stage and its application to materials characterization", Microsc. Microanal. Microstruct., 4, (1993), 127-135.
Kamino, T., et al., "In-situ high-resolution electron microscopy study on a surface reconstruction of Au-deposited Si at very high temperatures", Philosophical Magazine A, 75(1), (1997), 105-114.

(56) References Cited

OTHER PUBLICATIONS

Min, K.-H., et al., "Crystallization behaviour of ALD-Ta2O5 thin films: the application of in-situ TEM", Philosophical Magazine, 85(18), (Jun. 21, 2005), 2049-2063.
Saka, H., "In situ observation of solid-liquid interfaces by transmission electron microscopy", J. Mater. Res., 20(7), (Jul. 2005), 1629-1640.
Saka, H., "In-situ TEM observation of transformation of dislocations from shuffle to glide sets in Si under supersaturation of interstitials", Philosophical Magazine, 86(29-31), (Oct.-Nov. 2006), 4841-4850.
Tsukimoto, S., et al., "In situ high resolution electron microscopy/electron energy loss spectroscopy observation of wetting of a Si surface by molten Al", Journal of Microscopy, 203(Pt 1), (Jul. 2001), 17-21.
Wu, Yiying, et al., "Direct Observation of Vapor-Liquid-Solid Nanowire Growth", J. Am. Chem. Soc., 123, (Mar. 13, 2001), 3165-3166.
"European Application Serial No. 12853899.8, Extended European Search Report mailed Jun. 29, 2015", 9 pgs.
"European Application Serial No. 12853965.7, Extended European Search Report mailed Nov. 16, 2015", 10 pgs.
"European Application Serial No. 12853965.7, Non Final Office Action mailed Sep. 9, 2015", 5 pgs.
"Japanese Application Serial No. 2012-541077, Office Action mailed Jan. 6, 2015", W/ English Translation, 4 pgs.
"Japanese Application Serial No. 2012-541077, Response filed Apr. 2, 2015 to Office Action mailed Jan. 6, 2015", W/English Translations, 13 pgs.
"Japanese Application Serial No. 2012-541077, Response filed Jun. 17, 2014 to Office Action mailed Mar. 18, 2014", with English translation of claims, 10 pgs.
"Japanese Application Serial No. 2014-543623. Voluntary Amendment filed Jul. 29, 2014", W/ English Claims, 18 Pgs.
"Japanese Application Serial No. 2014-543624, Voluntary Amendment filed Jul. 29, 2014", W/ English Claims, 14 pgs.
"Japanese Application Serial No. 2015-517243, Final Office Action mailed Dec. 1, 2015", W/ English Translation, 5 pgs.
U.S. Appl. No. 13/510,825, filed Jul. 30, 2012, Micro Electro-Mechanical Heater.
U.S. Appl. No. 13/090,036, filed Apr. 19, 2011, Indenter Assembly.
U.S. Appl. No. 14/361,133, filed May 28, 2014, High Temperature Heating System.
U.S. Appl. No. 14/361,094, filed May 28, 2014, High Temperature Heating System.
"U.S. Appl. No. 14/361,094, Non Final Office Action mailed Nov. 15, 2016", 9 pgs.
"U.S. Appl. No. 14/361,094, Response filed Oct. 31, 2016 to Restriction Requirement mailed Aug. 31, 2016", 11 pgs.
"U.S. Appl. No. 14/361,133, Final Office Action mailed Nov. 3, 2016", 13 pgs.
"U.S. Appl. No. 14/361,133, Response filed Oct. 12, 2016 to Non Final Office Action mailed Apr. 15, 2015", 15 pgs.
"U.S. Appl. No. 14/948,549, Non Final Office Action mailed Oct. 26, 2016", 8 pgs.
"U.S. Appl. No. 14/361,094 Restriction Requirement mailed Aug. 31, 2016", 7 pgs.
"Japanese Application Serial No. 2015-202642, Office Action mailed Sep. 6, 2016", (With English Translation), 4 pgs.
"European Application Serial No. 12853965.7, Communication Pursuant to EPC Article 94(3) mailed Oct. 13, 2016", 3 pgs.
"European Application Serial No. 13804048.0, Response filed Sep. 7, 2016 to Extended European Search Report mailed Feb. 9, 2016", 39 pgs.

"Japanese Application Serial No. 2014-543623, Office Action mailed Oct. 4, 2016", W/ English Translation, 10 pgs.
"Japanese Application Serial No. 2014-543624, Office Action mailed Oct. 4, 2016", W/ English Translation, with English Translation, 9 pgs.
"U.S. Appl. No. 13/510,825, Corrected Notice of Allowance mailed Mar. 7, 2016", 2 pgs.
"U.S. Appl. No. 14/361,133, Non Final Office Action mailed Apr. 15, 2016", 10 pgs.
"European Application Serial No. 13804048.0, Extended European Search Report mailed Feb. 9, 2016", 6 pgs.
"European Application Serial No. 12853899.8, Response filed Dec. 9, 2016 to Office Action mailed May 30, 2016", 15 pgs.
"European Application Serial No. 12853965.7, Response filed Feb. 16, 2017 to Communication Pursuant to Article 94(3) EPC mailed Oct. 13, 2016", 12 pgs.
"Japanese Application Serial No. 2014543623, Response filed Mar. 3, 2017 to Office Action mailed Oct. 4, 2016", w/English Claims 9 pgs.
"Japanese Application Serial No. 2015-202642, Response filed Dec. 5, 2016 to Office Action mailed Sep. 6, 2016", w/ English Claims, 8 pgs.
"Japanese Application Serial No. 2016-074111, Office Action mailed Dec. 12, 2016", w/English Translation, 6 pgs.
"U.S. Appl. No. 13/510,825, Notice of Allowance dated Aug. 28, 2015", 8 pgs.
"Japanese Application Serial No. 2015-517243, Office Action dated Jun. 16, 2015", W/ English Translation, 9 pgs.
"Japanese Application Serial No. 2015-517243, Response filed Sep. 4, 2015 to Office Action dated Jun. 16, 2015", W/ English Translation, 21 pgs.
"U.S. Appl. No. 14/361,094, Final Office Action dated Apr. 20, 2017", 7 pgs.
"U.S. Appl. No. 14/361,094, Response filed Apr. 4, 2017 to Non final Office Action dated Nov. 15, 2016", 20 pgs.
"U.S. Appl. No. 14/361,133, Notice of Allowance dated Jun. 5, 2017", 9 pgs.
"U.S. Appl. No. 14/361,133, Response filed May 3, 2017 to Final Office Action dated Nov. 3, 2016", 13 pgs.
"U.S. Appl. No. 14/948,549, Notice of Allowance dated Mar. 22, 2017", 12 pgs.
"European Application Serial No. 12853899.8, Communication Pursuant to Article 94(3) EPC dated Mar. 17, 2017", 7 pgs.
"U.S. Appl. No. 14/361,094, Examiner interview Summary dated Jul. 26, 2017", 3 pgs.
"U.S. Appl. No. 14/361,094, Non Final Office Action dated Jul. 31, 2017", 4 pgs.
"U.S. Appl. No. 14/361,094, Response filed Jul. 20, 2017 to Final Office Action dated Apr. 20, 2017", 13 pgs.
"U.S. Appl. No. 14/361,133, Corrected Notice of Allowance dated Aug. 14, 2017", 4 pgs.
"U.S. Appl. No. 14/948,549, PTO Response to Rule 312 Communication dated Aug. 14, 2017", 2 pgs.
"Japanese Application Serial No. 2014-543624, Examiners Decision of Final Refusal dated Aug. 22, 2017", with English Translation, 6 pgs.
"Japanese Application Serial No. 2016-074111, Response filed Aug. 1, 2017 to Office Action dated Dec. 12, 2016", with English Translation, 20 pgs.
"European Application Serial No. 12853899.8, Response filed Sep. 27, 2017 to Communication Pursuant to Article 94(3) EPC dated Mar. 17, 2017", 13 pgs.
"U.S. Appl. No. 14/361,133, Corrected Notice of Allowance dated Oct. 5, 2017", 4 pgs.

\* cited by examiner

ENVIRONMENTAL CONDITIONING ASSEMBLY FOR USE IN MECHANICAL TESTING AT MICRON OR NANO-SCALES

CLAIM OF PRIORITY

This patent application is a U.S. National Stage Filing under 35 U.S.C. 371 from International Patent Application Serial No. PCT/US2013/031650, filed Mar. 14, 2013, published on Dec. 19, 2013 as WO 2013/187972 A1, which claims the benefit of priority to U.S. Provisional Patent Application Ser. No. 61/659,391, filed on Jun. 13, 2012, all of which are incorporated herein by reference in their entirety.

TECHNICAL FIELD

This document pertains generally, but not by way of limitation, to environmental control adjacent a sample subject to micron or nano-scale mechanical testing.

BACKGROUND

Measuring mechanical properties of micro or nano-structural samples is of importance as more modern devices utilize materials and structures at these scales. Micron and nano-mechanical characterization is used to measure and evaluate numerous mechanical properties of materials, including modulus, hardness, fracture toughness, wear resistance and friction coefficients. Nanoindentation has proven to be a method to reveal mechanical properties and sample behavior at scales of microns or less (e.g., micron and nano-scales). Nanoindentation quantitatively measures mechanical properties, such as elastic modulus and hardness, of materials at these scales. In nanoindentation, a nanoindenter capable of determining the loading force and displacement is used.

One variable in predicting material behavior is the evaluation of structures and their material properties while the structures are heated. Hot hardness testing has been used at macro and micron scales previously with some drawbacks, as discussed herein. One of the major problems in testing at elevated temperature is the thermal drift and long term thermal stability of the system. A major source of thermal drift is fluctuations in the temperature of the load frame over time.

In some examples, heating stages are built so the sample material is heated using a macro scale resistive heating stage with very large surface area compared to the test probe dimensions. The tip of the mechanical testing instrument is brought in contact with the specimen surface with a contact force and the probe is allowed to heat passively through the sample. When the probe and the sample system reach a steady state, the thermal drift reaches a steady state and the indentation testing (or other deformation based testing) is carried out. A major problem with this approach is the significant amount of time needed to reach the steady state temperature between each testing procedure. Although thermal drift reaches a steady state where measurements can be done in a few seconds, the drift rates are much higher, making the measurements very unreliable for longer time indents (e.g., around ten seconds or longer). Additionally, the entire volume of the instrument chamber is heated (including the instrument, instrument housing, stage assembly and the surrounding chamber walls encompassing these components).

In other examples atomic force microscopes utilize a cantilever with a heated tip. In this system the cantilever deflection is measured as the tip temperature is increased. The deflection is then used to identify the melting transition. This is a qualitative approach and may only provide a relative estimate of the cantilever penetration for different regions, but does not give any quantitative information.

Another issue with high temperature heating of a sample involves oxidation of one or more of the probe tip, the sample or the sample stage. With high temperature heating, for instance above 80 degrees Celsius, the materials of these components may oxidize and accordingly affect the mechanical properties of testing instruments and stage as well as the sample being tested. Oxidation (or other temperature based chemical reactions) frustrate the accurate and reliable measuring of mechanical characteristics of the samples under consideration.

OVERVIEW OF THE DISCLOSURE

In order to extend mechanical property mapping and micron and nano-scale characterization of samples to higher temperatures (e.g., up to about 1500 degrees Celsius), an environmental conditioning assembly (e.g., including a housing) localized around the sample to be tested is described herein. The environmental conditioning housing is configured to condition the environment around the sample, as well as the sample itself, for testing according to one or more specified conditions. For instance, the environmental conditioning assembly (including the housing) described herein is configured to condition the environment of the sample (e.g., the sample stage and the probe tip), and the sample itself by one or more of heating, cooling, application of inert or mixed gases, introduction or removal of humidity and the like. The environmental condition assembly allows the practitioner to perform micron and nano-scale mechanical characterization of micron and nano-scale structures, particles and devices according to one or more of these desired conditions in a small environment localized around the sample. Accordingly, environmental conditioning of significantly larger volumes and materials (e.g., an overall instrument chamber, microscope, indenter and the like) is avoided. Steady state temperatures at the sample and the probe tip are thereby reached more rapidly and are more accurately controlled because of the smaller localized environment (e.g., local to the sample and the probe tip).

Additionally, by providing a controlled environment around the sample, the sample is tested at elevated temperatures without causing chemical reactions in the sample (or probe) that could otherwise alter the material make up. For instance, by introducing an inert gas into the environmental cavity within the housing, the sample is isolated from an oxidizing environment (e.g., air) and is accordingly tested at an elevated temperature while reducing the risk of oxidation.

Furthermore, the environmental condition assembly includes in another option an expansion and contraction linkage that substantially ensures the sample, and a sample surface of the sample stage remain at a static elevation during heating and cooling (relative to an initial steady state configuration). In one example, the expansion and contraction linkage includes supports, such as jacket supports, that support the bottom jacket, and stage supports that support and position the sample stage relative to the bottom jacket. While the sample is heated, for instance with a sample heater associated with the sample stage, the jacket supports and stage supports expand relatively upward and the bottom jacket expands in an opposed direction (e.g., relatively downward during heating) to offset the upward expansion. The net result is the elevations of the sample and the sample stage surface remaining substantially static. In a similar manner the expansion and contraction linkage operates to hold the sample stage static during cooling according to reversed contraction of these components.

The micron and nano-scale characterization techniques usable with the environmental conditioning chamber include, but are not limited to, indentation, scratch testing, tribology testing, tensile testing, compression testing, dynamic tests using amplitude and phase data for mechanical property measurements, and modulus mapping.

This overview is intended to provide an overview of subject matter of the present disclosure. It is not intended to provide an exclusive or exhaustive explanation of the subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
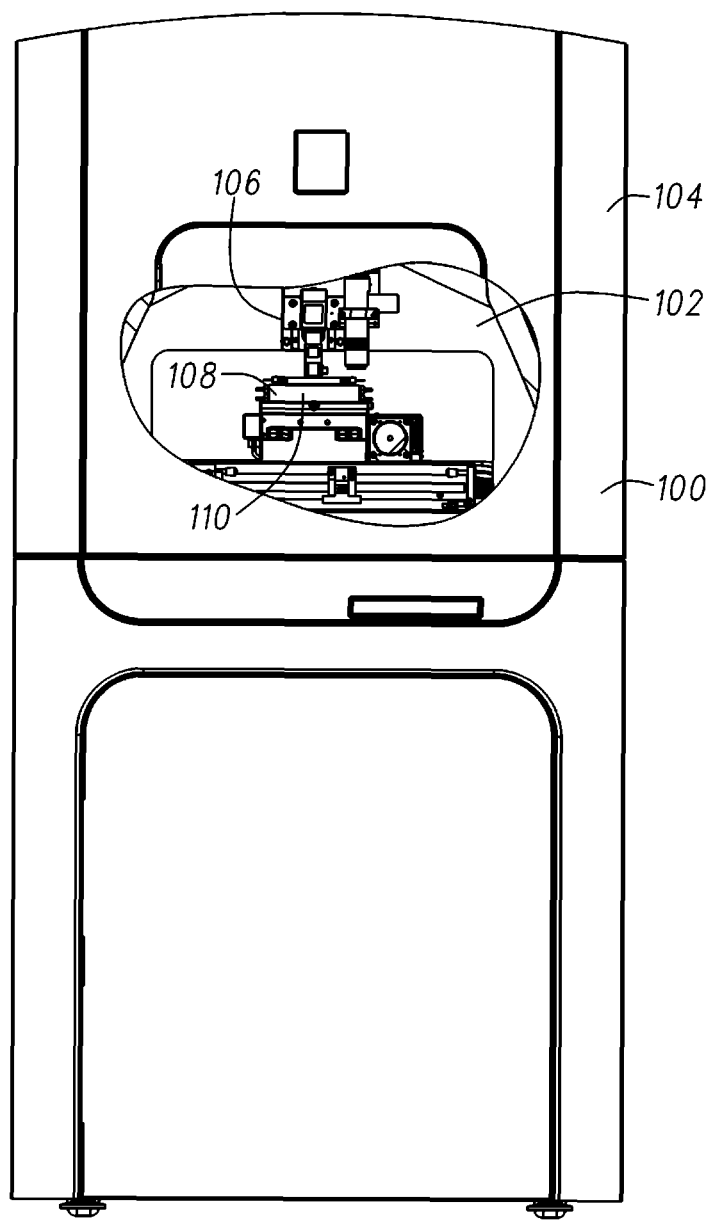
FIG. 1 is a perspective view of one example of a testing instrument assembly including a localized environmental conditioning assembly therein.

FIG. 1 shows one example of a testing instrument assembly 100. As shown, the testing instrument assembly 100 includes an instrument chamber 102 formed by an instrument housing 104. The instrument chamber 102 includes a testing instrument 106 provided therein. In one example, the testing instrument 106 includes a probe configured to extend through an environmental conditioning assembly 108, for instance through an enclosure housing 110, and accordingly engage and measure characteristics of a sample positioned within the housing 110.

The environmental conditioning enclosure 108 is shown below the testing instrument 106. As shown, the environmental conditioning assembly 108 includes the enclosure housing 110 providing an environmental cavity therein. The environmental cavity provides a space for a stage as well as a sample positioned on the stage. That is to say, the sample is positioned within the environmental cavity and is accordingly surrounded by the walls of the enclosure housing 110. Stated another way, the enclosure housing 110 is clustered around the sample positioned within the enclosure housing 110 and accordingly a perimeter of the enclosure housing such (e.g., a cavity perimeter) is immediately adjacent to and surrounds the sample to minimize the volume of the environmental cavity relative to a volume of the instrument chamber 102.

As will be described in detail herein, the environmental conditioning assembly 108 provides a conditioned localized environment for the sample therein. As shown for instance in FIG. 1, the instrument chamber 102 has a volume much larger than the volume of the environmental cavity within the enclosure housing 110. Accordingly, the environmental cavity of the enclosure housing 110 is quickly conditioned, including, but not limited to, heating, cooling or conditioning with one or more fluids (e.g., gases or liquids) and the like to provide a desired environment for a sample during testing (e.g., with the testing instrument 106). Stated another way, the environmental conditioning assembly 108 provides a localized environment isolated from the remainder of instrument chamber 102. Accordingly, heating, cooling, environmental conditioning and the like are localized to the sample and accordingly are not distributed throughout the instrument chamber 102. Additionally, the sample within the enclosure 108 is isolated from an exterior environment including undesired conditions and fluctuations for instance changes in temperature, humidity, atmosphere composition or the like in the area surrounding the testing instrument assembly 100 (and within the instrument chamber 102). Testing of the sample is thereby readily conducted under one or more desired environmental conditions without interaction with the surrounding environment including the instrument chamber 102 or an environment surrounding the testing instrument assembly 100 (e.g., ambient atmosphere or the like).

Figure 2:
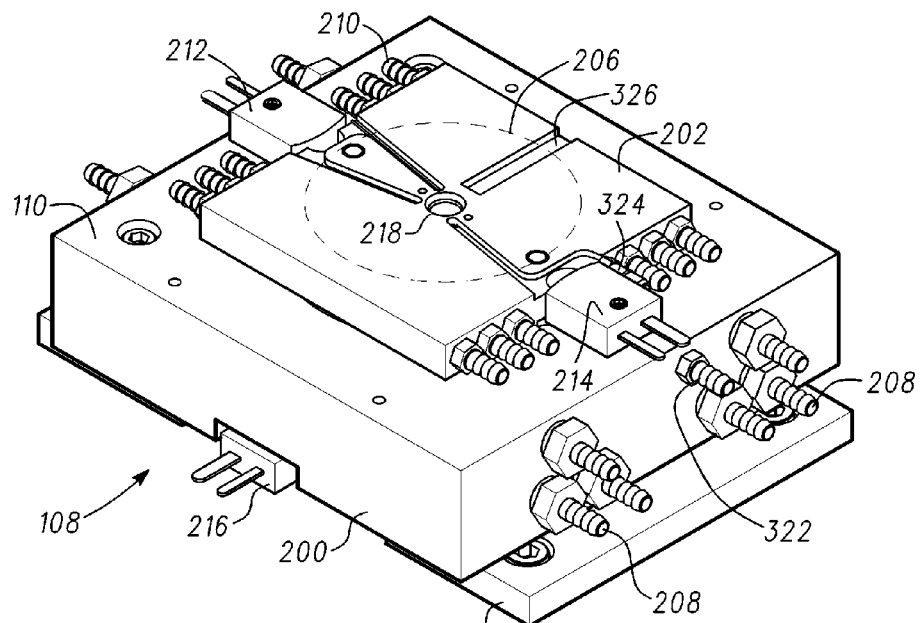
FIG. 2 is a perspective view of one example of an environmental conditioning assembly.

Referring now to FIG. 2, one example of the environmental conditioning assembly 108 is provided. As previously described, the environmental conditioning assembly 108 includes an enclosure housing 110. In one example, the enclosure housing 110 includes a bottom jacket 200 and a top jacket 202 coupled together to form the environmental cavity 206 therein. As further shown in FIG. 2, in one example, the enclosure housing 110 is coupled with a base plate 204. As will be described herein the base plate provides a support to the enclosure housing 110, for instance, by way of one or more posts (e.g., jacket supports that support the bottom jacket 200 and accordingly support the remainder of the enclosure housing 110).

The housing 110 (e.g., the enclosure housing) includes a testing instrument access port 218 extending to the environmental cavity 206 and providing access to a sample within the cavity. In one example, the testing instrument access port 218 is sized and shaped to permit the passage of an instrument, such as a probe of the testing instrument 106 therethrough. The testing instrument access port 218 is dimensioned to facilitate free movement of a probe within the port (e.g., vertically along a Z axis and optionally along one or more of X or a Y lateral axes). Accordingly, the access port 218 provides a gap between an instrument extending through port and the inner perimeter of the port. The testing instrument access port 218 provides access to the sample, while the remainder of the housing 110 maintains the desired environment within the cavity 206.

The environmental conditioning assembly 108, for instance through the testing instrument access port 218, provides ready access to a sample with the environmental cavity 206 for one or more testing instruments configured to conduct a variety of tests. In one example, the testing assembly 106 or another testing assembly used with the environmental conditioning assembly 108 is operable to conduct one or more of micro or nano indentation, compression testing, attractive force measurement testing, scratch testing, wear testing, material fracture testing, in-situ topography imaging, creep testing, dynamic mechanical testing and all within the controlled environment provided by the assembly 108.

As previously described, the housing 110 is configured to provide an isolated environment to a sample within the environmental cavity 206. In one example, heat transfer to and from the environmental cavity 206 is throttled through a combination of one or more of active heating or cooling, material selection of the housing 110 and insulation and minimizing access to the environmental cavity (e.g., through a limited number of orifices or ports). As shown in the example of FIG. 2, the housing 110 includes cooling inlets and outlets 208, 210 in one or both of the bottom and top jackets 200, 202. In one example, a cooling or heating fluid is provided through the inlets and outlets 208, 210 and corresponding passages extending through one or both of the bottom and top jackets 200, 202.

In one example, the fluid conducted through the inlets and outlets 208, 210 is a cooling fluid configured to accordingly cool the bottom and top jacket 200, 202 for instance to room temperature while the sample within the environmental cavity 206 is heated for instance with one or both of a sample heater or a top heater as described herein. In another example, where a sample is cooled within the environmental cavity 206, for instance with a refrigerant or other chilled fluid pumped through the environmental cavity 206, the inlets and outlets 208, 210 of the bottom and top jackets 200, 202 are used to conduct a heated fluid through passages in the jackets to maintain the jackets 200, 202 at a desired temperature (e.g., room temperature). Expansion and contraction of the housing 110 (and nearby components of the testing instrument 106) and thermal mechanical drift are accordingly minimized.

In another example, thermal insulation materials, such as a ceramic foam is included within the housing 110 to isolate the housing (constructed in one example with copper bottom and top jackets 200, 202) from heating or cooling of the sample within the environmental cavity 206.

Referring again to FIG. 2, as shown the environmental conditioning assembly 108 includes a plurality of interfaces configured to operate one or more of heaters or sensors positioned within or adjacent to the environmental cavity 206. For instance, the top jacket 202 includes a top heater interface 212 sized and shaped to provide electrical connection with the top heater associated with the top jacket 202. In another example, the top jacket 202 includes a sensor interface 214. In one example, the sensor interface 214 includes one or more thermocouple leads coupled to a thermocouple in the top heater coupled with the top jacket 202. In another example, the sensor interface 214 is coupled with another temperature sensor (or other type of sensor) provided within the environmental cavity 206. In a similar manner, the bottom jacket 200 includes in one example a bottom heater interface 216 (and bottom sensor interface). As will be described herein the bottom heater interface 216 is coupled with a sample heater provided with a sample stage. Optionally, the bottom jacket 200 includes another interface, in a similar manner to the top jacket 202, configured to provide a sensor interface to a temperature sensor or other sensor associated the environmental conditioning assembly 108.

As previously described and shown in FIG. 2, in one example, the environmental conditioning assembly 108 includes a baseplate 204. One example of the baseplate 204 is sized and shaped for coupling with a stage surface of an overall instrument, such as the testing instrument assembly 100. The baseplate 204 provides a solid kinematic base for the housing 110 and accordingly allows for accurate positioning of the environmental conditioning assembly 108 with regard to the testing instrument 106. By coupling the baseplate 204 with a translational stage (e.g., of the testing instrument assembly 100) the enclosure 108 and the testing instrument access port 218 are movable to accurately align the testing instrument access port with a probe of the testing instrument 106. The solid base provided by the baseplate 204 minimizes lateral movement of the testing instrument access port 218 (e.g., shaking caused by translation of the enclosure 108) and ensures that an instrument delivered through the port does not undesirably engage the port perimeter. In another example, the baseplate 204 is coupled with a static stage of the testing instrument assembly 100 and the testing instrument 106 is otherwise movable relative to the testing instrument access port 218 to align a probe with the access port.

Figure 3:
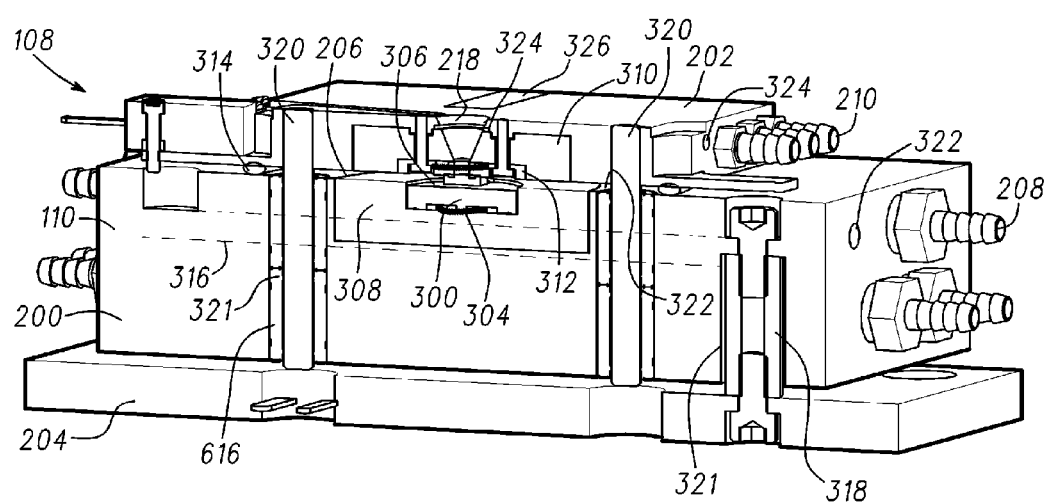
FIG. 3 is a first cross sectional view of the environmental conditioning assembly of FIG. 2.

FIG. 3 shows a cross-sectional view of the housing 110 previously shown in FIG. 2. The housing 110 includes a sample stage 300 positioned within a portion of the bottom jacket 200. The sample stage 300 includes a stage surface 306 sized and shaped to receive a sample thereon. As further shown in FIG. 3, the sample stage 300 further includes a sample heater 304 localized to the sample stage 300 (for instance potted within the stage) and thereby able to readily heat a sample positioned on the sample stage 300. A bottom insulation ring 308 is in one example interposed between the sample stage 300 and the remainder of the bottom jacket 200 to accordingly throttle heat transfer from the sample stage 300 to the remainder of the bottom jacket 200. Accordingly the sample stage 300 in combination with the sample heater 304 provides localized heating to a sample positioned on the stage surface 306.

Optionally, a top heater 312 coupled with the top jacket 202 is provided in close positional relationship relative to the sample stage 300. That is to say, within the environmental cavity 206 the sample heater 304 and the top heater 312 are positioned in close proximity with a sample positioned on the sample stage surface 306. As will be described herein, in one example the sample stage 300 cooperates with the top heater 312 to provide clamping with surface to surface contact for a sample positioned therebetween. Accordingly, a sample positioned between the sample stage 300 and the top heater 312 receives conductive heating from both the top heater 312 and the sample heater 304 to provide consistent thorough heating throughout the sample and accordingly substantially minimize sample temperature gradients. In another example, the sample heater 304 and the top heater 312 are heated to different temperatures and thereby providing a desired heating gradient within the sample. The sample may be tested with either of these scenarios according to a consistent temperature or a desired temperature gradient provided by the sample heater 304 and the top heater 312 according to the desires of the testing technician.

As further shown in FIG. 3, a top insulation ring 310 is in one example interposed between the top heater 312 and the remainder of the top jacket 202 to accordingly throttle heat transfer from the top heater 312 to the remainder of the top jacket 202. The bottom and top insulation rings 308, 310 cooperate to thermally isolate the sample stage 300, the top heater 312 and a sample on the sample stage from the remainder of the environmental conditioning assembly 108. Accordingly, the sample heater 304 provided with the sample stage and the top heater 312 provide localized heating (or cooling) to a sample positioned on the stage surface 306 while the remainder of the housing 110 is insulated from such heater (or cooling).

The sample heater 304 (and the top heater 312) heat samples within the environmental cavity 206 over a range of temperatures. In one example, one or more of the sample heater 304 and the top heater 312 are configured to reach temperatures (and accordingly heat samples) of at least 1500 degrees Celsius. In another example, one or more of the sample heater 304 and the top heater 312 are configured to reach temperatures of 500, 750, 1000, 1200 degrees Celsius or the like. The environmental conditioning assembly 108 through one or more mechanisms constrains heating (and cooling as well) to the enclosure cavity 206 through insulation within the cavity 206 (such as foam ceramic insulation found in the bottom and top insulation rings 308, 310), active cooling (or heating) of the housing 110 through the cooling or heating inlets and outlets 208, 210 and passages within the housing. Accordingly, even at the high temperatures generated with the heaters 304, 312 heating is localized to the sample, and heat transfer is substantially throttled to the remainder of the housing 110 as well as the environment exterior to the housing 110.

As further shown in FIG. 3, a jacket seal 314 is provided around the environmental cavity 206. The jacket seal 314 is in one example provided by a deflectable material, such as silicone rubber or another material configured to withstand extremely high temperatures generated within the environmental cavity while at the same time maintaining the seal between the top and bottom jackets 202, 200. In one example the jacket seal 314 includes, but is not limited to, silicone, fluorocarbon elastomers, PTFE, flexible metal (e.g., a bellows type seal or the like. As shown in FIG. 3, the jacket seal 314 encircles at least a portion of the environmental cavity 206 and accordingly seals the environmental cavity (excepting the testing instrument access port 218 and the optional environmental conditioning inlets and outlets described herein).

As previously described, the enclosure housing is optionally formed as a two part assembly including the bottom and top jackets 200, 202. In one example, one or more guideposts 320 extending from one or the other of the top or bottom jackets 202, 200 are sized and shaped for reception within corresponding passages 321 provided within the bottom jacket 200. As will be described herein, in one example, the passages 321 include linear bearings. The linear bearings provide a snug movable engagement with the guideposts 320 and thereby constrain movement of the top jacket 202 as the top jacket is coupled with the bottom jacket 200. For instance, the guidepost 320 are slidably received within the linear bearings of the passages 321 and accordingly guide the top jacket 202 downwardly as the top jacket is lowered into engagement with the jacket seal 314 to close the environmental cavity 206. The gradual lowering of the top jacket 202 (e.g., with the guideposts 320 and the passages 321) constrains lateral movement of the top jacket 202 and accordingly facilitates downward movement along a Z axis. Accordingly, as the top heater 312 moves downward toward the sample stage 300 and a sample positioned on the stage surface 306 the top heater 312 is able to engage with the sample provided on the sample stage 300 in surface to surface contact without relative lateral movement between the sample and the top heater 312. The sample is accordingly retained between the sample stage 300 and the top heater 312 through vertical clamping with substantially no appreciable lateral movement between either of the samples stage 300 or the top heater 312 relative to a sample clamped therebetween.

In another example, the environmental conditioning assembly 108 provides an expansion and contraction linkage configured to maintain a sample at a desired elevation, for instance, while the sample is heated or cooled at a steady state temperature. As will be described herein during heating of the sample, for instance, to steady state temperatures (e.g., 1500 degrees Celsius), minor fluctuations with regard to voltage applied to the sample heater 304 and the top heater 312 result in corresponding fluctuations of heating of the sample and the sample stage 300. The corresponding fluctuations in temperature provide dynamic elevation changes through expansion, contraction, thermomechanical drift and the like to the components of the environmental conditioning assembly 108. Accordingly, measurement errors caused by these fluctuations may be introduced to testing procedures conducted with the testing instrument 106 shown in FIG. 1.

The expansion and contraction linkage (described in further detail herein) minimizes these elevation changes caused by fluctuation from the steady state temperature. In one example, the expansion and contraction linkage includes a plurality of components shown in FIG. 3 and further described herein. For instance, in one example, the linkage includes an interface member 316 provided between an interface for one or more jacket supports 318 as well as one or more stage supports provided between the sample stage 300 and the interface member 316. The jacket supports 318, the interface member 316, as well as the stage supports (further described herein) cooperate during heating or cooling of a sample positioned on the sample stage 300 to correspondingly minimize elevational changes caused by fluctuations from a steady state temperature.

As previously described herein, the environmental condition enclosure 108 facilitates the localized conditioning of an environment around a sample, for instance, a sample positioned on the sample stage 300. The environmental cavity 206 provides a compact localized environment allowing for one or more of heating or cooling of a sample positioned on the sample stage 300, as well as the introduction of one or more conditioning fluids through one or more ports provided within the housing 110. Referring to FIG. 3, in one example, an environmental conditioning inlet 322 is provided in one or more of the bottom and top jackets 200, 202. The environmental conditioning inlet 322 shown in FIG. 3 extends to and is communication with the environmental cavity 206 and is accordingly able to deliver one or more gases, fluids or the like (inert, reactive, heated, cooled or the like) to the environmental cavity 206. The introduction of these fluids conditions the environment within the environmental cavity 206 according to the desired testing parameters.

In another example, the top jacket 202 as shown in FIG. 3 includes an environmental conditioning outlet 324. The environmental conditioning outlet 324 provides a return outlet for fluids delivered into the environmental cavity 206, for instance by way of the environmental conditioning inlet 322 previously described. In still another example, a gas delivery channel 326 is provided along the top jacket 202 to provide inert gas delivery to the testing instrument access port 218. Optionally, the inert gas delivery conditions the environment local to the testing instrument access port 218 as well as an instrument probe extending therethrough. The gas delivery channel 326 is used in at least one example to condition fluids exiting the environmental cavity 206 to substantially prevent undesirable cooling or heating of a probe shaft or a transducer coupled with the probe shaft otherwise caused by heating or cooling within the environmental cavity 206.

In one example, the environmental conditioning inlet 322 is configured to provide a flow of an inert gas into the environmental cavity 206 including, but not limited to, argon, nitrogen or some combination of gases such as argon and hydrogen. The inert gas is provided to the environmental cavity 206 and accordingly the sample disposed therein to provide a non-oxidizing environment for the sample. In one example, where the sample stage 300 is heated for instance with the sample heater 304 and the top heater 312 the environment within the environmental cavity 206 reaches high temperatures (e.g., 1500 degrees Celsius). In an otherwise ambient atmosphere high temperatures may oxidize the sample and accordingly undesirably change its mechanical properties prior to testing with the testing instrument 106 shown in FIG. 1. Accordingly, it is of interest to provide a non-oxidizing environment to the environmental cavity 206. The environmental conditioning inlet 322 provides one means for introducing inert gases and other environmental control fluids into the environmental cavity 206. In one example, the environmental conditioning inlet 322 provides an inert gas as described above. In another example the inert gas 322 provides one or more of a heating or cooling fluid to the environmental cavity 206 that correspondingly heats or cools the environment provided within the environmental cavity 206 while at the same time also heating or cooling the sample positioned on the sample stage 300.

As further shown in FIG. 3, the environmental conditioning outlet 324 provided optionally in the top jacket 202 is used in one example to remove fluid from the environmental cavity 206. For instance the environmental conditioning outlet 324 and the environmental conditioning inlet 322 cooperate to provide a flow of fluids into the environmental cavity 206 throughout a testing procedure for a sample positioned on the sample stage 300. In addition to providing inert gases, heated and cooled fluids and the like, in one example the environmental conditioning inlet 322 is used to provide other conditioning fluids to the environmental cavity 206. For instance, the fluid provided to the environmental cavity 206 in one example is a humidified stream of gas provided from a chamber of humidified gas in communication with the environmental conditioning inlet 322.

In another example, the gas delivery channel 326 is configured to provide a flow of gas to the testing instrument access port and accordingly interrupts a flow of fluid from the environmental cavity 206 otherwise extending through the testing instrument access port 218 possibly rising along a probe shaft toward a transducer of the testing instrument 106 shown in FIG. 1. The gas delivery channel 326 in one example provides a stream of cooled gas (such as an inert cooled gas) to the testing instrument access port 218 to substantially interrupt and prevent the upward flow of heated gases along a probe shaft. By interrupting the flow of heated gases along the probe shaft corresponding heating of sensitive instrumentation and transducers within the testing instrument 106 is substantially avoided.

The environmental conditioning assembly 108, as described herein, provides a large temperature drop between the sample stage 300 and the top heater 312 to the bottom and top jackets 200, 202. The temperature drop at the interface of the environmental cavity 206 to the housing 110 minimizes thermal expansion (or contraction with cooling) of the heating stage during the heating operation. Further, a steep temperature drop through the housing 110 also reduces the overall heated volume of the enclosure 108 and correspondingly the power needed for heating. Further still, by minimizing the heating (or cooling) of the enclosure 110 thermomechanical drift of the enclosure 108 is also minimized A steep temperature drop is realized by providing a large thermal resistance through the enclosure 108 using one or more of the bottom and top insulating rings 308, 310 or the heating or cooling inlets and outlets 208, 210 shown in FIG. 2.

Figure 4:
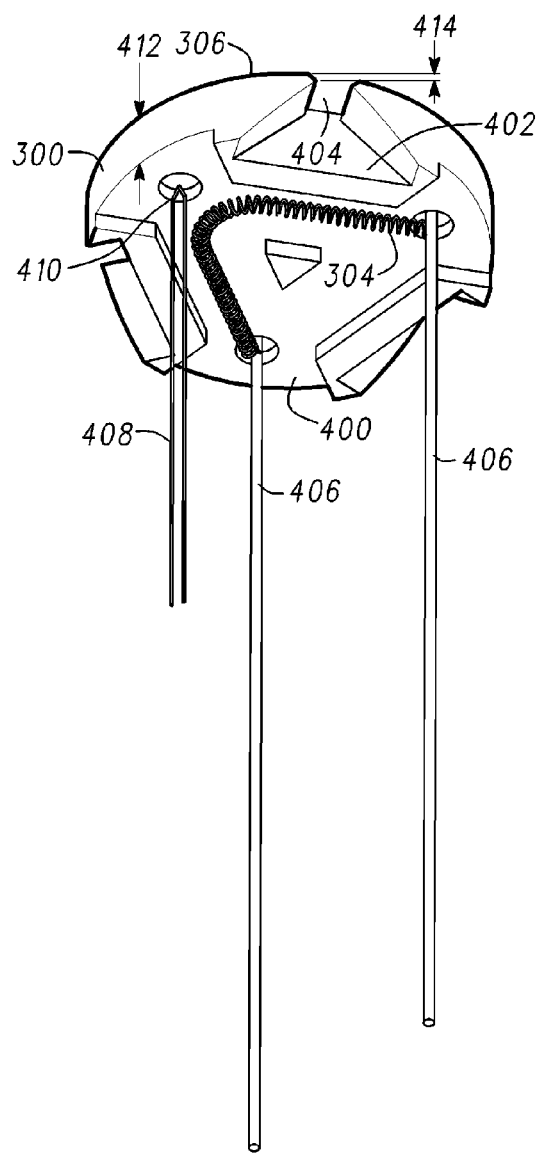
FIG. 4 is a perspective bottom view of one example of a sample stage including a sample heater.

Referring now to FIG. 4, one example of the sample stage 300 previously shown in FIG. 3 is provided. In the view shown in FIG. 4, the sample stage 300 is seen from below thereby exposing the sample heater 304 as well as a plurality of pin recesses 402 arranged around the sample stage 300. Referring first to the sample heater 304, the sample heater 304 includes a heating element extending between two or more heating element leads 406. As shown, the sample heater 304 (the heating element) is a wire coil configured for potting within the sample stage 300. The sample heater 304 accordingly provides heating to the sample stage 300 in a distributed fashion across the stage surface 306 to accordingly heat a sample positioned thereon. As further shown in FIG. 4, a stage thermocouple 410 is also provided with the sample stage 300. Thermocouple leads 408 extend from the thermocouple 410 for coupling with an interface extending from the bottom jacket 200 shown in FIG. 2. In a similar manner, the heating element leads 406 are coupled with a bottom heater interface 216 as shown in FIG. 2. By providing the sample heater 304 within the sample stage 300 heating of a sample within the environmental cavity 206 is substantially localized to the sample stage 300. Additionally, the pin recesses 402, described immediately below, constrain heat transfer by limiting the interface between the sample stage 300 and the underlying stage supports. For instance, the pin recesses 402 each have a tapered shape that provides two point contact (as opposed to surface to surface contact) between the sample stage and a stage support.

Referring again to FIG. 4, and as discussed above, the sample stage 300 includes a plurality of pin recesses 402. The tapered configuration of each of the pin recesses 402 is sized and shaped to receive a corresponding stage support therein. The tapered pin recesses 402 provide for at least two point engagement with each of the respective stage supports and accordingly provide stable support to the sample stage 300 at each of at least three locations along the stage. In one example, three pin recesses 402 are provided on the sample stage 300 to provide three point support for the sample stage 300 and accordingly a stable kinematic surface for the positioning and testing of samples on the stage surface 306.

As further shown in FIG. 4, in one example, the sample stage 300 has dual thicknesses. A first thickness 412 is measured between the stage surface 306 and an opposed stage surface 400 and a second thickness 414 is measured between the stage surface 306 and a recess trough 404 of the pin recess 402. As will be described herein, the second smaller thickness 414 of the sample stage 300 is used in one example to minimize the effect of thermomechanical drift and expansion or contraction of the sample stage 300 on testing of a sample coupled with the sample stage 300. The second thickness cooperates with operation of the expansion and contraction linkage described herein. For instance, the second thickness 414 corresponding to the distance between the recess trough 404 and the stage surface 306 substantially minimizes the expansion and contraction of the sample stage 300 during heating. By minimizing the second thickness 414 (corresponding to the location where the stage supports engage with the sample stage 300) any expansion or contraction of the sample stage 300 as it applies to elevation changes of the sample is limited to the second thickness 414 (and not the overall larger first thickness 412). The remainder of the sample stage, for instance, that portion of the stage 300 below the second thickness (e.g., the remainder of the first thickness) is substantially ignored during expansion or contraction as it extends remotely relative to the stage supports and otherwise provides no additive or subtractive elevation to the sample positioned on the stage surface 306.

In one example, the second thickness 414 is about zero (0) millimeters as the recess trough 404 is positioned immediately adjacent to or coincident with the stage surface 306. For instance, as shown in FIG. 4 the recess trough 404 opens onto the stage surface 306 thereby accordingly positioning an appropriately sized stage support positioned within the pin recess 402 immediately adjacent to the stage surface 306.

In one demonstrative example, the sample heater 304 is installed with the sample stage 300 by potting a heater wire into grooves on the back side of the sample stage 300. The grooves are optionally formed between the housings for each of the pin recesses 402. In one example, the sample stage 300 is constructed with, but not limited to, aluminum nitride. FIG. 4 shows the coiled heater wire of the sample heater 304 along the sample stage 300. The thermocouple 410 (such as a 0.005" wire diameter Type K; Part number CHAL-005 from Omega) is also potted within the groove. The heater wire is made from a material such as Nichrome or Kanthal configured to withstand high temperatures (e.g., temperatures of at least 1500 degrees Celsius) with minimal oxidation. As an additional measure to prevent oxidation, a refractory coating is optionally used to coat the heating element wires. The heater wire diameter of the sample heater 304 is between about 0.003 to 0.0035 inches, and the heater wire length is selected to provide a resistance of about 25 Ohms. The sample heater 304 (coiled heater wire) is attached to the larger heating element leads 406 with a crimping bead. In one example, the heating element leads 406 are also constructed with Nichrome or Kanthal are several times larger than the heater wire used in the sample heater 304 to minimize the resistive heating in the lead wires.

Figure 5:
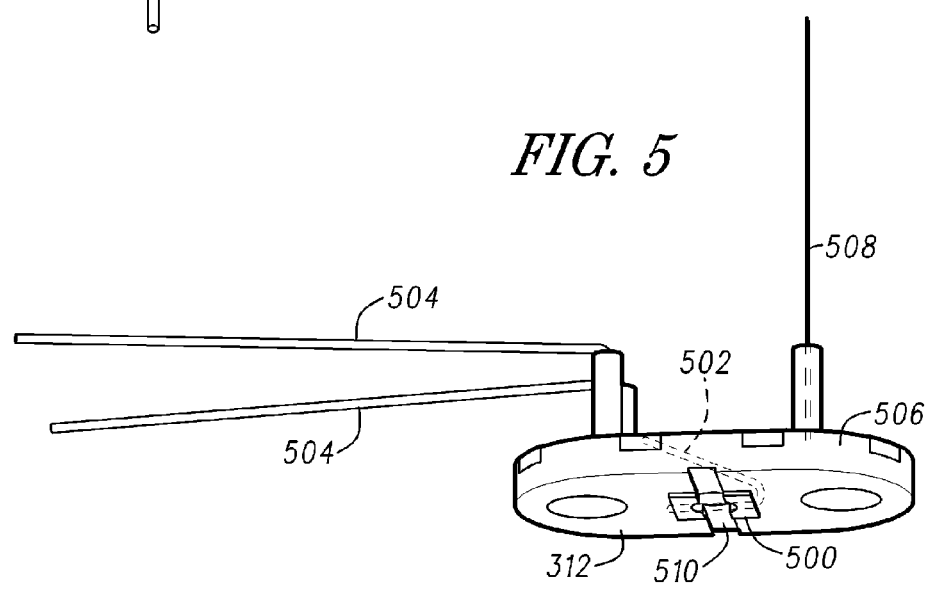
FIG. 5 is a perspective bottom view of one example of a top heater.

FIG. 5 shows one example of a top heater 312 (previously shown in FIG. 3). The top heater 312 includes a plurality of features similar in at least some regards to the sample stage 300 previously shown in FIG. 4. The top heater 312 includes a potted heating element 502. The heating element 502 in one example includes a wire coil coupled with heating element leads 504 extending away from the top heater 312 as shown in FIG. 5. Additionally, in another example a temperature sensor, such as a top heater thermocouple 506 is also positioned within the top heater 312. Thermocouple leads 508 extend away from the top heater thermocouple and are configured for coupling with the corresponding sensor interface 214 shown in FIG. 2. In a similar manner, the heating element leads 504 coupled with the top heater 312 are correspondingly configured for coupling with the top heater interface 212 also shown in FIG. 2.

Referring again to FIG. 5, the top heater 312 cooperates with the sample stage 300 to clamp a sample positioned therebetween in surface to surface contact. As shown in FIG. 5, in one example a clamping surface 500 is provided on the top heater 312. The clamping surface 500 is sized and shaped to correspondingly engage with the sample position on the sample stage 300. In one example, as the top jacket 210 is positioned and coupled with the bottom jacket 200, for instance by way of the guide posts 320 received within the passages 321 of the bottom jacket 200 (previously shown in FIG. 3), the top jacket 202 descends relative to the bottom jacket 200 until the clamping surface 500 engages with the sample and accordingly clamps the sample between the clamping surface 500 and the sample stage 300. Additionally, the descending top jacket 202 in one example engages with the jacket seal 314 extending between the top and bottom jackets 202, 200 to close the environmental cavity 206 and thereby provide the isolated environment for the sample within the environmental cavity 206.

In another example, the top heater 312 includes one or more fluid channels 510 extending across a portion of the top heater 312, for instance through the clamping surface 500. As shown in FIG. 5, the fluid channels 510 extend through the top heater 512 after extending laterally across the top heater toward the clamping surface 500. That is to say, the fluid channels 510 extend upwardly through the top heater 312 and are accordingly in communication with the testing instrument access port 218. Accordingly, as fluids are delivered to the environmental cavity 206, for instance, through the environmental conditioning inlet 322 (including one or more of heated or cooled fluids, environmental conditioning fluids, and the like) these fluids are delivered through the fluid channels 510 to accordingly condition substantially the entire environment of the environmental cavity 206 including that portion of the environmental cavity immediately above the sample on the sample stage 300. The conditioning fluids are thereafter delivered upwardly in one example through the testing instrument access port 218 and are removed with the environmental conditioning outlet 324.

In one demonstrative example, the top heater 312 is constructed with, but not limited to, aluminum nitride. As shown in FIG. 3, the top heater 312 is optionally surrounded by the insulation ring 310, for instance a ceramic foam material, such as Cotronics Rescor 310. The top heater 312 is retained within the top jacket 202 by fasteners, such as screws, pins, rivets or the like. Optionally, the fasteners are made of Zirconia having a low thermal conductivity to minimize heat transfer to the jacket 202.

Figure 6A:
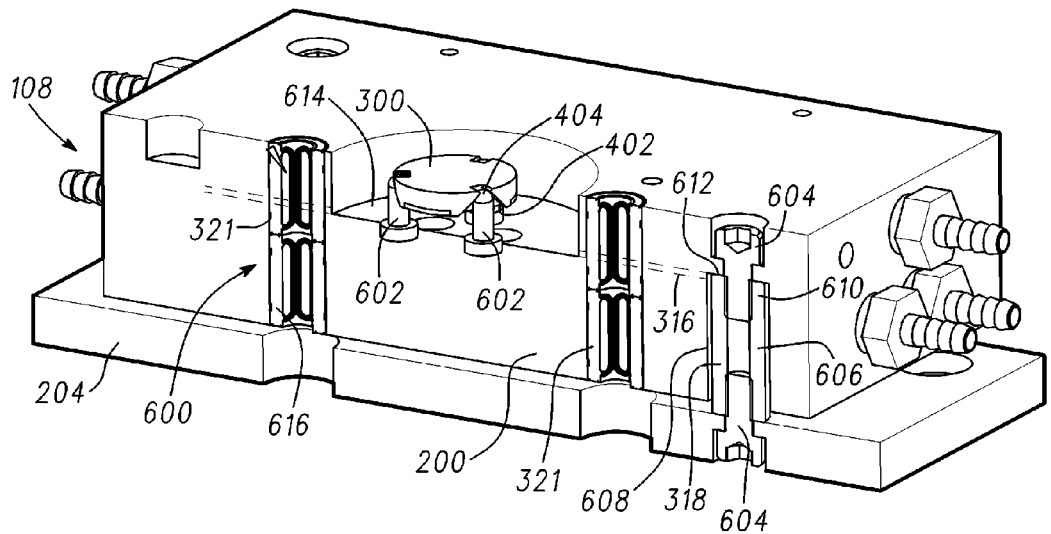
FIG. 6A is a perspective cross-sectional view of one example of an expansion and contraction linkage coupled with the sample stage.

FIG. 6A is a cross-sectional view of the environmental conditioning assembly 108 previously described herein. In the view shown in FIG. 6A, the top jacket 202 is removed to expose the bottom jacket 200 coupled with the base plate 204. In one example the bottom jacket 200 is suspended above the base plate 204 with a plurality of jacket supports 318 (e.g., interface supports). As shown, the jacket supports 318 have a length greater than the distance between the support interface 612 and the bottom of the bottom jacket 200. Accordingly, the jacket supports 318 suspend the bottom jacket 200 as well as the remainder of the enclosure housing 110 above the base plate 204. Stated another way, the housing 110 is substantially isolated from the remainder of the environmental conditioning assembly 108 by way of the jacket supports 318. The jacket support 318 accordingly throttle heat transfer from the housing 110 to the remainder of the environmental conditioning assembly 108, such as the base plate 204 as well as any features coupled with the base plate (for instance, one or more components of the testing instrument assembly 100).

Referring again to FIG. 6A, in the example an expansion and contraction linkage 600 is provided between the stage 300 and the base plate 204. In one example, the expansion and contraction linkage 600 includes the jacket supports 318, an interface member 316, and the plurality of stage supports 602 extending between the interface member 316 and the sample stage 300. The jacket supports 318 extend from the base plate 204 to a support interface 612 of the interface member 316. As will be described herein, in one example the interface member 316 extends from the support interface 612 to a stage interface 614 coupled with the stage support 602. As further shown in FIG. 6A, the stage supports 602, for instance support pins for the stage 300, extend upwardly from the stage interface 614 to support the stage 300. For instance, the stage supports 602 are received within the pin recesses 402 including recess troughs 404. The expansion and contraction linkage 600 accordingly provides a linkage extending from the sample stage 300 to the base plate 204. As described herein, the expansion and contraction linkage 600 maintains the elevation of the sample stage 300 and a sample thereon substantially static while the sample stage and the sample experience fluctuations in temperature that would otherwise cause elevational changes (and corresponding measurement error with an instrument engaged with the sample).

In one example, the interface member 316 is incorporated into and is part of the bottom jacket 200. For instance the interface member 316 is a portion of the bottom jacket 200 between the support interface 612 and the stage interface 614. As shown in the figure, the stage interface 614 is recessed relative to the support interface 612. In another example, the interface member 316 is separate from the bottom jacket 200. For instance, the interface member 316 is a separate component extending between the support interface 612 and the stage interface 614. Accordingly, in such an example the interface member 316 is a separate component from the bottom jacket 200 and is dedicated to the expansion and contraction of the linkage 600.

Referring again to FIG. 6A, the jacket supports 318 include a column body 606 extending between the base plate 204 and the support interface 612. In one example, the column body 606 outer diameter is smaller than a support cavity 608 inner diameter sized and shaped to receive the jacket supports 318 therein. The column body 606 when positioned within the support cavities 208 (and centered, for instance by one or more support posts 604, such as screws, pins or the like coupled with the jacket 200 and the base plate 204) provides a gap between the jacket support 318 and the bottom jacket 200. The gap between the jacket support 318 and the remainder of the bottom jacket 200 allows for independent movement of each of the jacket supports 318 as well as the interface member 316 during operation of the expansion and contraction linkage 600. Stated another way, the jacket 200 is isolated from at least the jacket supports 318 and accordingly does not interfere with expansion or contraction of the supports.

In another example and as previously described, the bottom jacket 200 includes linear bearings sized and shaped to receive the guidepost 320 therein. The cooperation of the guidepost 320 and the linear bearings 616 (e.g., within the passages 321) allows the top jacket 202 to easily descend toward the bottom jacket 200 due to gravity and accordingly close the environmental cavity 206. With regard to the expansion and contraction linkage 600, the guideposts 320 cooperate with the bottom jacket 200 to suspend the top jacket 202 upon the bottom jacket and accordingly ensure that the top jacket 202 does not interfere with operation of the expansion and contraction linkage 600.

Figure 6B:
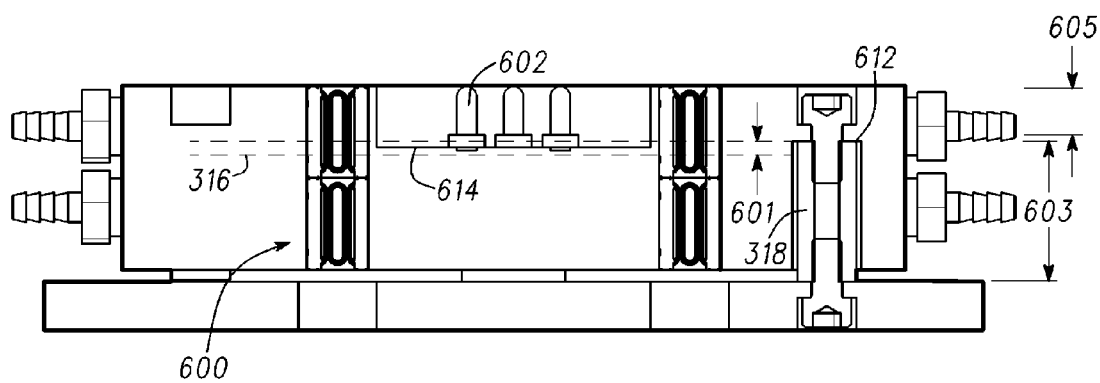
FIG. 6B is a cross-sectional view of the expansion and contraction linkage of FIG. 6A showing stage interface of the bottom jacket recessed relative to a support interface.

Referring now to FIG. 6B, the expansion and contraction linkage 600 is shown in a cross-sectional view. As previously described, in one example the expansion and contraction of the linkage 600 includes one or more stage supports 602, the interface member 316 coupled with the stage supports 602, and the jacket supports 318 also coupled with the interface member 316. As shown in FIG. 6B, the interface member 316 includes two components, for instance the support interface 612 sized and shaped to engage with the jacket supports 318 and the stage interface 614 sized and shaped to engage with the stage support 602. The stage interface 614 as shown is recessed a length 601 (e.g., about 1 mm) relative to the support interface 612. The jacket supports 318 and the stage supports 602 have corresponding lengths that cooperate with the recessed stage interface 614 to ensure a net elevation change of about 0 mm with expansion and contraction of the linkage 600 through heating or cooling within the housing 110 (of the housing itself), as described herein. In one example, the jacket supports 318 have lengths 603 of about 25 mm, and the stage supports 602 have lengths 605 of around 9.5 mm. The lengths in combination with the materials chosen for the components of the linkage minimize any elevation change.

The recessing of the stage interface 614 relative to the support interface 612 provides a cooperative counter movement to corresponding expansion and contraction of each of the stage supports 602 and the jacket supports 318. For instance, during heating of a sample, the stage supports 602 and the jacket supports 318 receive at least some measure of heat transfer from the sample stage 300 and accordingly expand upwardly relative to the stage interface 614 and the base plate 204, respectively. The expansion of the jacket supports 318 biases the support interface 612 upwardly. In contrast to the expansion of each of the stage supports 602 and the jacket supports 318, the interface member 316 expands in an opposite direction relative to the expansion of each of the stage supports 602 and the jacket supports 318 because stage interface 614 is relative to the support interface 612. For instance, with heating the interface member 316 expands downwardly relative to the upward expansion of the stage supports 602 and the jacket supports 318. The converse occurs with cooling in the environmental cavity. That is to say, the stage supports 602 and the jacket supports 318 contract in a first direction, while the interface member 316 contract in an offsetting second direction. Accordingly, the net translation of the expansion and contraction linkage 600 whether during heating or cooling at a steady state temperature is a net elevation change of 0 with fluctuations from the steady state temperature.

Accordingly, where the sample stage 300 is heated (or cooled) to a steady state temperature and temperature fluctuations occur through one or more of voltage fluctuations in the sample heater 304, the top heater 312 or variations in a coolant fluid provided to the environmental cavity 206, the expansion and contraction linkage 600 operates to offset expansion or contraction otherwise generated by these temperature fluctuations at the stage surface 306. Accordingly, the sample elevation on the sample stage 300 as shown in FIG. 6A remains substantially static even with fluctuations in temperature relative to a steady state temperature (whether heated or cooled). Measurements, for instance measurements conducted with the testing instrument 106 of the testing instrument assembly 100, are thereby conducted with a substantially static sample (when heated or cool) as opposed to a sample that moves based on temperature fluctuations from a desired steady state temperature.

Figure 7:
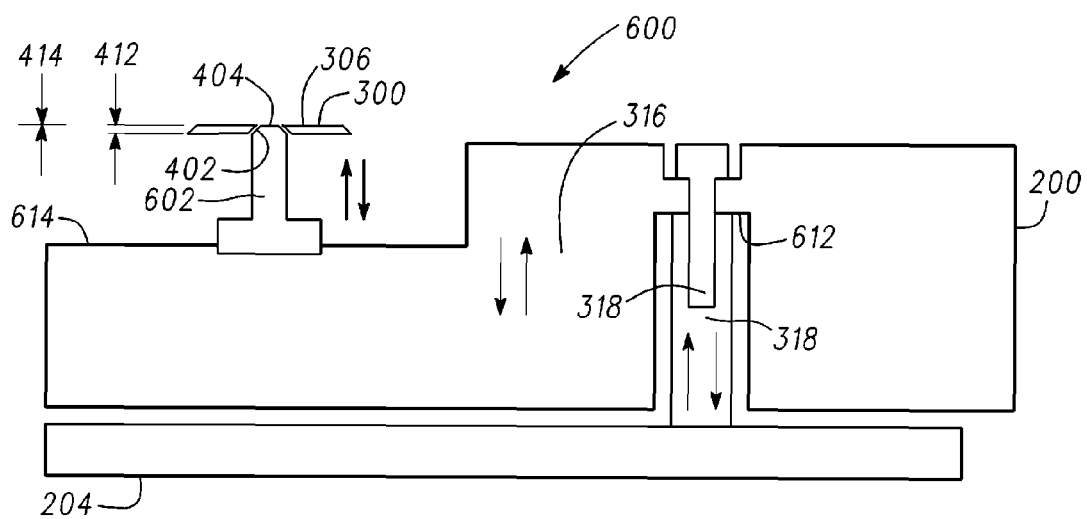
FIG. 7 is a schematic view of the expansion and contraction linkage of FIG. 6A.

FIG. 7 shows a schematic view of the expansion and contraction linkage 600 previously described and shown in FIGS. 6A and 6B. In the schematic view the left most arrows of each pair of arrows associated with the stage supports 602, interface member 316, and the jacket supports 318 corresponds to of at least the sample stage 300 along with incidental heat transfer to the remainder of the housing 110. The right most arrows of the paired arrows for each of the stage supports 602, the interface member 316 and the jacket supports 318 corresponds to cooling of the stage 300 and optionally the environmental cavity 206 for instance through the provision of a chilled or cooled fluid provided by the environmental conditioning inlet 322 (as shown in FIG. 3). As shown, the downward movement of the interface member 316 in the heated condition offsets the corresponding upward movement provided by the stage supports 602 and the jacket supports 318 caused by expansion of each of these components. In a similar fashion, the upward relative movement of the interface member 316 offsets the corresponding downward movement of the stage support 602 and the jacket supports 318 during cooling within the environmental cavity 206 caused by contraction of each of these components of the linkage 600.

The materials of each of the stage supports 602, jacket supports 318, as well as the interface member 316 (for instance, the bottom jacket 200) are chosen according to their thermal mechanical properties including their coefficients of thermal expansion, thermal conductivities, and the like. Through material selection and the configuration of the linkage shown herein including dimensional relationships between each of the jacket supports 318, the interface member 316, and the stage support 602, the interface member 316 is able to offset expansion and contraction of both of the stage supports 602 and the jacket supports 318 during either of heating or cooling. That is to say, the interface member 316 moves in an opposite direction relative to the stage supports 602 and the jacket supports 318 and is able to offset expansion or contraction of these features and accordingly maintain the stage surface 306 with the sample thereon at a desired elevation (for instance as the state 300 is subjected to temperature variations from a steady state temperature).

In another example, the sample stage 300 includes the recess troughs 404 positioned immediately adjacent to the stage surface 306 (also shown in FIG. 4). Placing the recess troughs 404 in close proximity to the stage surface 306 ensures expansion or contraction of the sample stage 300 and a corresponding elevation change of the surface 306 is substantially mitigated or minimized by the close and intimate engagement of the stage supports 602 at the stage surface 306. That is to say, the second thickness 414 (also shown in FIG. 4) is substantially minimized by providing the recess troughs 404 immediately adjacent to the stage surface 306 or coincident with the stage surface 306. Accordingly, expansion or contraction of the sample stage 300 during heating or cooling is correspondingly minimized with regard to its effect on the sample elevation (e.g., has a minimal effect on operation of the expansion and contraction linkage 600). The expansion and contraction linkage 600 as described herein is thereby able to maintain the stage surface 306 and a sample positioned thereon at a substantially static elevation even with temperature fluctuations from a steady state temperature.

In one example, the expansion and contraction linkage 600 shown in FIGS. 6A, B is a demonstrative example having the characteristics provided in the expansion and contraction equations provided below. As previously described, the interface member 316 minimizes the Z-Displacement of the stage supports 602 and the jacket supports 318 caused by heating or cooling relative to a steady state temperature. As the interface member 316 changes temperature ($\Delta T$), the average temperature change of the stage supports 602 is about half of the temperature change of the interface member 316 because the temperature at the top end of the stage supports is controlled by the sample stage 300 temperature. The average temperature change of the jacket supports 318 is also about half of the temperature change of the interface member 316 (e.g., optionally the bottom jacket 200) because the temperature of the bottom ends of the jacket supports 318 is determined by the temperature of the underlying base plate 204. The Z-displacement caused by a temperature change in the environmental conditioning assembly 108 (and attenuated by the expansion and contraction linkage 600) is the sum of the Z-displacements of the stage supports 602, the interface member 316 and the jacket supports 318. The dimensions and materials for each these components are selected so that the Z-displacements sum to approximately zero. The jacket supports 318 are made of a low coefficient of thermal expansion material including, but not limited to, Invar. The interface member 316 (e.g., the bottom jacket 200) is made of copper and has a moderate coefficient of thermal expansion relative to the other components. The stage supports 602 are constructed with, but not limited to, Quartz having a low coefficient of thermal expansion relative to at least interface member 316.

$$Z\text{-Displacement}=\Delta T*\text{Length}*\text{Coefficient of Thermal Expansion}$$

$$\text{Jacket Supports (material: invar)}=\tfrac{1}{2}\Delta T*25\text{ mm}*1.2\text{ ppm/}°\text{ C.}=15\text{ nm/}°\text{ C.}$$

$$\text{Interface Member (material: copper)}=\Delta T*-1\text{ mm}*17\text{ ppm/}°\text{ C.}=-17\text{ nm/}°\text{ C.}$$

$$\text{Stage Supports (material: quartz)}=\tfrac{1}{2}\Delta T*9.4\text{ mm}*0.5\text{ ppm/}°\text{ C.}=2.4\text{ nm/}°\text{ C.}$$

The net displacement across the linkage 600 (e.g., through each of the components) at the top of the stage supports 602 is approximately 0.4 nm per degree Celsius within the environmental conditioning assembly 108.

Figure 8:
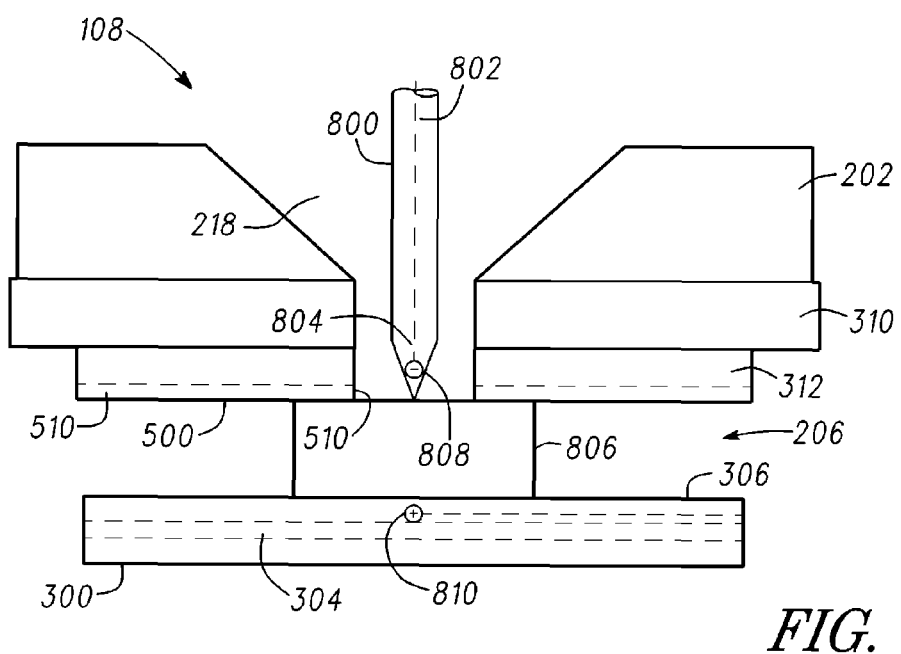
FIG. 8 is a schematic view of the top and bottom jackets clamping a sample therebetween.

FIG. 8 shows a schematic view of a portion of the environmental conditioning assembly 108. As shown in FIG. 8, the top jacket 202 is coupled along a portion of a sample 806 provided on the sample stage 300. As further shown in the figure the sample 806 is clamped between the top jacket 202, for instance the top heater 312, and the sample stage 300 including the sample heater 304 therein. As previously described the clamping engagement of the sample 806 provides surface to surface contact with the sample 806 and accordingly facilitates conductive heat transfer at both opposed surfaces of the sample 806 corresponding to the interfaces with the top heater 312 and the stage surface 306 (the sample heater 304 is optionally within the sample stage 300).

As previously described, in one example, the top jacket 202 includes one or more guideposts 320 sized and shaped for reception within passages 321 of the bottom jacket 200. In another example, linear guide bearings 616 are provided in the passages 321 and are configured to snuggly receive the guideposts 320 therein and guide the top jacket 202 along a substantially vertical axis into engagement with the sample 806 as shown in FIG. 8. Accordingly, as the top heater 312 engages with the sample 806 (e.g., at the clamping surface 500 previously shown in FIG. 5) the top heater 312 provides substantially no lateral movement to the sample 806. Accordingly, the sample 806 is stably engaged by the top heater and clamped between the sample stage 300 and the clamping surface 500 with substantially no lateral movement imparted to the sample 806. In another example, a fixation feature such as a spring clamp or the like is applied to the top and bottom jackets 202, 200 to further immobilize the clamping engagement between the top heater 312 and the sample stage 300. In another example, the construction of the bottom and top jackets 200, 202 for instance with copper plates affirmatively clamps the sample 806 between the top heater 312 (e.g., included in the top jacket 202 and the sample stage 300 provided in the bottom jacket 200) due to gravity.

Referring again to FIG. 8, as previously described the top heater 312 in at least one example includes a plurality of fluid channels 510. The fluid channels 510 allow for communication between the testing instrument access port 218 and the remainder of the environmental cavity 206. For instance, where an environmental conditioning fluid is supplied to the environmental cavity 206, for instance by the environmental conditioning inlet 322 shown in FIG. 3, the environment provided in the environmental cavity 206 extends into the testing instrument access port 218 (e.g., the portion of the environmental cavity 206) immediately above the sample 806. Accordingly, the entirety of the sample 806 is maintained within the environment of the environmental cavity 206. A probe 800, for instance of the testing instrument 106 shown in FIG. 1, extends through the testing instrument access port 218 to engage with the sample 806. Because the environment of the environmental cavity 206 is provided in the testing instrument access port 218, the probe 800 engages the sample 806 within that provided environment (e.g., heated, cooled, conditioned with one or more fluids or the like). Stated another way, the testing instrument access port 218 in in communication with and is part of the environmental cavity 206.

As previously described, in one example the clamping engagement between the top heater 312 and the stage 300 is configured to provide consistent reliable heating throughout the sample 806. For instance, the surface to surface contact provided by the clamping engagement readily conducts heat into the sample 806. Where the top heater 312 and the sample heater 304 are heated to the same temperature the sample 806 has a substantially minimized temperature gradient between the opposed surfaces engaged with the top heater 312 and the sample stage 300. In another example, the top heater 312 and the sample heater 304 are heated to varying degrees. For instance, the top heater 312 is heated to a first temperature while the sample heater 304 is heated to a second temperature different from the first temperature of the top heater 312. In such an example, the clamped sample 806 is provided with a gradient of temperatures from its top most surface adjacent to the clamping surface 500 to its bottom most surface adjacent to the stage surface 306. Accordingly where it is desirable to measure properties of the sample according to temperature gradients therein such a temperature gradient is provided by the clamping engagement achieved with engagement of the top heater 312 and the sample stage 300 with the sample 806.

As further shown in FIG. 8, in one example, the probe 800 includes one or more electrical contacts 808 at the probe tip 804. Similarly the sample stage 300 includes one or more corresponding electrical contacts 810. As shown, the electrical contacts 808, 810 are configured to engage the sample 806 held in clamping engagement between the top heater 312 and the sample stage 300. In one example, the testing instrument 106 previously shown in FIG. 1 is used in cooperation with the sample stage 300 to perform one or more electrical characteristic tests of the sample 806. For instance, a potential is applied across the contact 808 of the probe 800 and the contact 810 of the sample stage 300 to accordingly measure one or more electrical characteristics of the sample 806 including but not limited to resistivity, conductivity, and the like.

Figure 9:
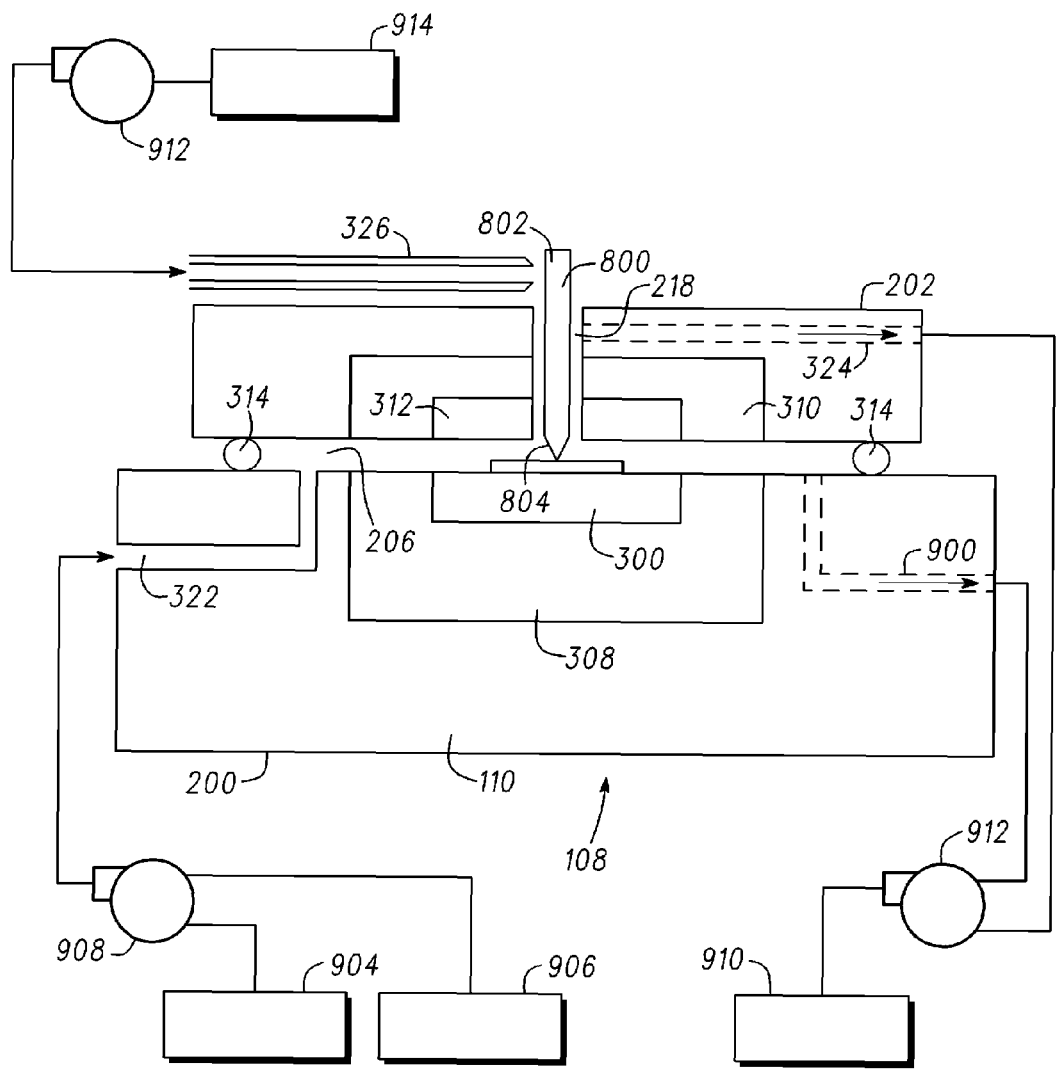
FIG. 9 is a schematic diagram of the environmental conditioning assembly showing a plurality of environmental condition features in communication with an environmental cavity having the sample therein.

FIG. 9 shows a schematic example of the environmental conditioning assembly 108. As previously described, the environmental conditioning assembly 108 provides a housing 110 having an environmental cavity 206. In the example shown in FIG. 9, the housing 110 includes bottom and top jackets 200, 202 coupled along a jacket seal 314. As shown, the environmental cavity 206 substantially isolates a sample within the environmental cavity while still providing access through a testing instrument access port 218. Additionally, the environmental cavity localizes a small environment to the area immediately adjacent to the sample, for instance by clustering the cavity perimeter of the enclosure housing 110 closely around the sample. With regard to the instrument chamber 102 of the testing instrument assembly 100 shown in FIG. 1, the instrument chamber volume 102 is significantly larger than the corresponding volume of the environmental cavity 206. Accordingly, conditioning of the environment within the environmental cavity 206 is readily accomplished through one or more inlets or outlets providing environmental conditioning fluid as well as localized heating or cooling of the sample positioned on the sample stage 300 without corresponding heating and temperature fluctuations caused in larger environments (e.g., volumes larger than the cavity 206).

As shown in FIG. 9, in one example, an environmental conditioning system is provided. The environmental conditioning system extends through the environmental cavity 206, for instance by way of the environmental conditioning inlet 322 and one or more environmental conditioning outlets 324, 900. In one example, an environmental conditioning outlet 324 is provided within the top jacket 202, for instance adjacent to the testing instrument access port 218. The environmental conditioning outlet 324 optionally applies a negative pressure (e.g., a vacuum) within the testing instrument access port 218 and accordingly prevents the egress of fluids from within the environmental cavity 206. In another example, an environmental conditioning outlet 900 is provided on the opposed side of the environmental cavity 206 relative to the environmental conditioning inlet 322. The environmental conditioning outlet 900 facilitates the delivery of environmental conditioning fluids within the environmental cavity 206 and across a sample on the sample stage 300 to further ensure the environmental cavity 206 and the sample are exposed to heating or cooling fluids and any other environmental conditioning fluids delivered between the inlet 322 and the outlet 900.

Referring again to FIG. 9, one example of a plurality of environmental conditioning fluid reservoirs for conditioning the environmental cavity 206 are provided. In one example, a coolant or heating fluid source 904 is provided in communication with the environmental conditioning inlet 322. The coolant or heating fluid source 904 includes a cooled or heated source of gas, liquid or the like provided at a desired temperature. The fluid is delivered by way of a conditioning pump 908 in communication with the environmental conditioning inlet 322. The conditioning pump 908 includes, but is not limited to, a pump, blower, fan, dripping mechanism, or the like.

In another example, the environmental conditioning loop includes a conditioning fluid source 906 (e.g., in communication with the conditioning pump 908). The conditioning fluid source 906 includes, but is not limited to, one or more reservoirs of inert gas, air, reactive fluids, liquids, humidified gases and the like. For instance, in one example the conditioning fluid source 906 includes a source of inert gas, such as a mixture of argon and hydrogen. As the inert gas is pumped (with the conditioning pump 908) into the environmental cavity 206 the surrounding environment of a sample therein is accordingly filled with the inert gas. As the sample is heated, for instance, by way of one or more of the sample heater 304 (within the sample stage 300) or the top heater 312 the environment within the environmental cavity 206 correspondingly elevates in temperature for instance to a temperature of 1500 degrees Celsius. With the inert gas present in the environmental cavity 206 oxidation of a sample on the sample stage 300 is substantially minimized. Accordingly, the testing of the sample (e.g., with the probe 800) is carried out in this elevated temperature without risk of oxidation of the sample therein.

In another example, the conditioning fluid source 906 provides a source of humidified gas for instance a bubbled inert gas delivered through a bath of chilled water. In another example, the conditioning fluid source 906 provides a source of a reactive fluid configured to initiate a chemical reaction with the sample in the environmental cavity 206. Accordingly by delivering the reactive fluid into the environmental cavity 206 the reaction with the sample is localized and accordingly the probe 800 is able to examine the reacting sample within a small localized environment substantially isolated from environmental factors exterior to the environmental conditioning assembly 108.

As further shown in FIG. 9, in one example, one or both of the environmental conditioning outlets 324, 900 are in communication with an extraction pump 912 and an extraction reservoir 910. The extraction pump 912, in one example, provides a negative pressure at one or more of the environmental conditioning outlets 324, 900. Accordingly, the environmental conditioning fluid provided by way of the environmental conditioning inlet 322 is drawn through the environmental cavity 206. Optionally, a flow of environmental conditioning fluid is delivered at a constant flow rate through the environmental cavity 206 to substantially maintain the environment around the sample positioned on the sample stage 300. For instance, one or more of heating or cooling of the sample is provided and continuously maintained throughout a testing procedure according to the needs of the procedure (e.g., cooling to subfreezing temperatures or heating to temperatures approaching 1500 degrees Celsius). In one example where the environmental conditioning outlet 324 is positioned within the testing instrument access port 218 the outlet 324 is configured to withdraw any fluids provided by way of the environmental conditioning inlet 322 prior to egress of the fluid through the access port 218.

For accurate testing and measurements at desired temperatures (e.g., cooled or heated) a sample within the environmental conditioning assembly 108 must be maintained at the desired temperature during testing, for instance while engaged by the probe 800. With the sample maintained at a desired temperature (e.g., 1500 degrees Celsius) prior to testing engagement of the probe 800 with the sample, if unheated, causes a significant temperature drop as heat is transferred to the probe based on contact area and the relative difference in temperatures. The temperature distribution from the sample to the probe 800 depends on the relative heat resistance through these components. The narrow heat flux through the very small contact area (e.g., where the probe tip 804 engages the ample) provides a large thermal resistance (thermal resistance is inversely proportional to the area perpendicular to the heat flux). The large heat resistance near the contact area causes a large temperature drop at the contact area of the sample and in the nearby vicinity. The temperature of the contact zone upon engagement with the probe tip 804 is not the same as the overall sample temperature.

Accordingly, heating of the probe is used to minimize this heat transfer and accordingly maintain a sample at the desired temperature. As shown in FIG. 9, the probe 800 (e.g., of the testing instrument 106 shown in FIG. 1) extends into the environmental cavity 206 by way of the testing instrument access port 218. In one example, for instance, where a sample is heated on the sample stage 300 by one or more of conductive heating provided through the sample heater 304 the top heater 312 or convective heating or cooling provided through the environmental conditioning inlet 322 it is desirable in at least some circumstances that the probe tip 804 is correspondingly heated to an identical temperature. In one example, by positioning the probe tip 804 within the environmental cavity 206 the probe tip 804 is readily heated to an identical temperature to the sample positioned on the sample stage 300. For instance, with the top heater 312 the bottom heater 304 and the sample positioned therebetween an environment is created locally around the probe tip 804 that correspondingly heats the probe tip 804, by radiation, to a temperature substantially identical to that of the sample on the sample stage 300. In another example where an environmental conditioning fluid such as heating or cooling fluids are provided through the environmental conditioning inlet 322 (or a fluid is heated by one of the heaters 304, 312) the environment within the environmental cavity 206 is correspondingly heated or cooled to a desired temperature. With the probe tip 804 positioned within the environment of the environmental cavity 206 the probe tip is correspondingly convectively heated or cooled to the same desired temperature.

Accordingly, upon engagement between the probe tip and the sample positioned on the sample stage 300 the probe tip 804 (when previously positioned within the environmental cavity 206) is at a substantially identical temperature. Accordingly heat transfer between the probe tip 804 and the sample on the sample stage 300 is substantially minimized. Instead, each of the probe tip 804 and the sample are at substantially the same temperature and accordingly the sample is tested at that elevated temperature without corresponding heat transfer from or to the probe tip 804. The sample thereby remains at the desired temperature throughout the testing procedure.

In another example, the environmental conditioning assembly 108 includes a gas delivery channel 326 configured to provide a flow of gas to the probe 800. As previously described, in one example the probe 800 is coupled with sensitive electronics and measurement equipment in the testing instrument 106 (e.g., capacitive transducers, sensors and the like) that are sensitive to changes in temperature for instance provided by heating of the sample on the sample stage 300. The gas delivery channel 326 in one example interrupts the flow of heated fluid upwardly from the environmental cavity 206 (e.g., along the probe shaft of the probe 800) and toward the transducers of the testing instrument 106. For instance, as shown in FIG. 9, the gas delivery channel 326 is coupled with an isolation fluid pump 912 and an isolation fluid source 914. In one example, the isolation fluid source 914 provides a heated or cooled flow of fluid (or optionally a room temperature flow of gas) that is pumped by way of the isolation fluid pump 912 to the transversely mounted gas delivery channel 326. The flow of gas from the gas delivery channel 326 crosses the probe shaft 802 of the probe 800 and accordingly interrupts the upward flow of any heated fluids from the testing instrument access port 218. That is to say, incidental flow of environmental conditioning fluids (such as gases, heated or cooled fluids, and the like) rising from the testing instrument access port 218 is interrupted by the flow of fluid from the gas delivery channel 326. Accordingly sensitive electronics, transducers and the like associated with the testing instrument 106 are preserved from the heated or cooled environment of the environmental cavity 206.

Figure 10:
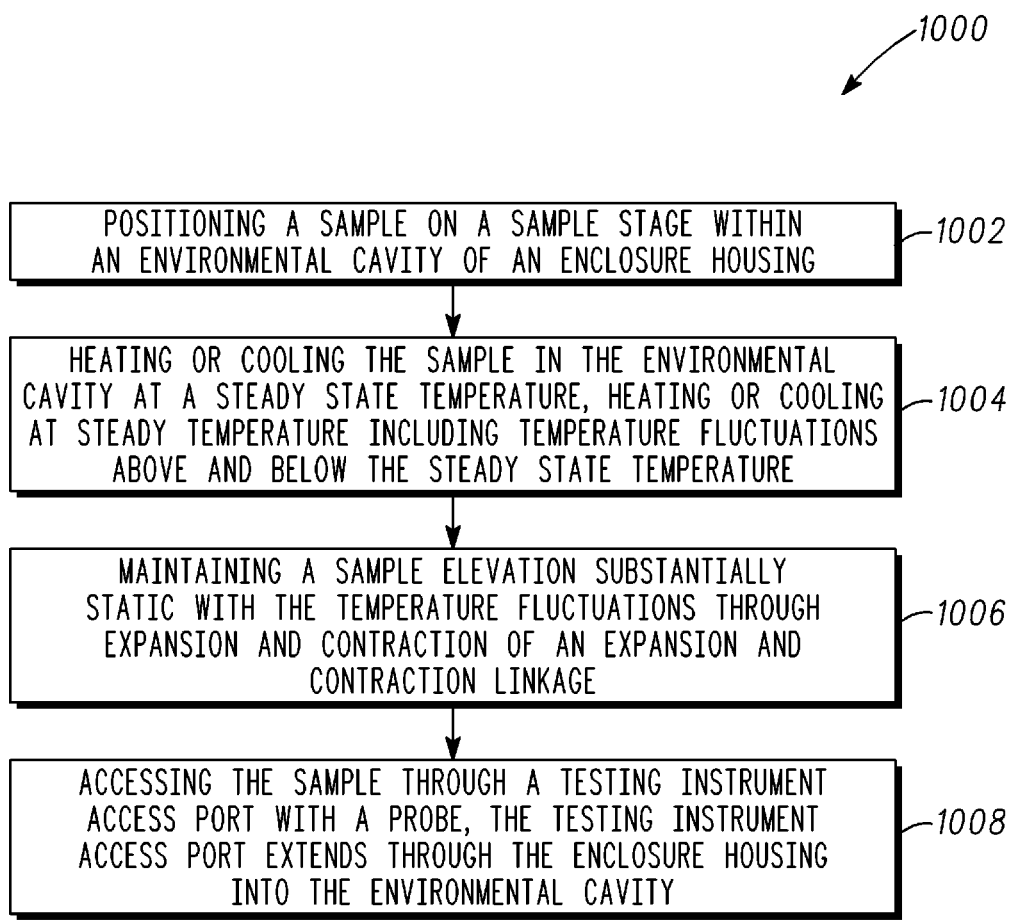
FIG. 10 is a block diagram showing one example of a method for using an environmental conditioning assembly.

FIG. 10 shows one example of a method 1000 for using an environmental conditioning assembly, such as the environmental conditioning assembly 108 shown in FIGS. 1 and 2. In describing the method 1000 reference is made to one or more components, features, functions, steps and the like described herein. Where convenient, reference is made with reference numerals. The reference numerals provided are exemplary and are not exclusive. For instance, the features components, functions, steps and the like described in the method 1000 include but are not limited to the corresponding numbered elements, other corresponding features described herein (both numbered and unnumbered) as well as their equivalents.

At 1002, the method 1000 includes positioning a sample such as the sample 806 on a sample surface (e.g., a stage surface 306) of a sample stage 300 within an environmental cavity 206 of a housing 110 (e.g., an enclosure housing 110). The cavity perimeter of the housing 110 is clustered around the sample stage 300 and the sample. For instance, in one example, the cavity perimeter corresponds to the inner perimeters of one or more of the top and bottom jackets 202, 200 closely arranged around the sample stage 300. Accordingly, the localized environment provided around the sample is small relative to a relatively open environment, for instance of the instrument chamber 102 shown in FIG. 1.

At 1004, the sample is heated or cooled in the environmental cavity 206 to a steady state temperature with a sample heating or cooling system. In one example, the sample heating or cooling system includes one or more of conductive convective and radiative systems of heating or cooling. For instance, in one example, the sample is conductively heated with a sample heater 304 and optionally a top heater 312 each of which is positioned in close proximity to the sample, for instance in clamping engagement. In another example, heating or cooling is provided by way of an environmental conditioning fluid delivered for instance through the environmental conditioning inlet 322 and removed through an environmental conditioning outlet (e.g., the outlets 324, 900 shown in FIG. 9). In one example, heating or cooling of the sample to the steady state temperature includes the sample experiencing temperature fluctuations above and below the steady state temperature, for instance caused by fluctuations in voltage, fluctuations in temperature in the environmental conditioning fluid and the like.

At 1006, the method 1000 includes maintaining a sample elevation and stage surface 306 elevation within the environmental conditioning assembly 108 substantially static with the temperature fluctuations provided during heating or cooling. In one example the elevations are maintained statically through expansion and contraction of an expansion and contraction linkage 600 shown in FIGS. 6A and 6B. As previously described herein, in one example the expansion and contraction linkage 600 is coupled between the housing 110 and the sample stage 300.

At 1008, the method 1000 includes accessing the sample through a testing instrument access port 218 with a probe 800. The testing instrument access port 218 extends through the housing 110 and into the environmental cavity 206. An access port perimeter of the testing instrument access port extends around the testing instrument positioned within the testing instrument access port and accordingly includes an actuation gap therebetween to facilitate movement of the probe 800, for instance during mechanical testing procedures involving movement of the probe to engage and deform the sample positioned within the environmental cavity 206. Accordingly, the testing instrument access port 218 maintains the isolation provided by the environmental cavity 206 to the sample while at the same time allowing interaction between a probe extending from the exterior of the environmental conditioning assembly 108 to the sample positioned within the cavity 206.

Several options for the method 1000 follow. In one example the method 1000 includes clamping a sample, such as the sample 806, between the top jacket and the bottom jacket of the housing 110. In another example, the top jacket and the bottom jacket 202, 200 include the top heater 312 and the sample stage 300. The sample 806 is clamped between the top heater 312 and the sample stage 300 to thereby provide conductive heat transfer from the top heater 312 and the sample stage 300 to the sample 806 from opposing surfaces.

As described, the environmental conditioning assembly 108 in one example includes an expansion and contraction linkage 600. In one example, the expansion and contraction linkage 600 includes a first portion that moves in a first direction during heating or cooling and a second portion of the linkage 600 that expands in a second opposed direction during heating or cooling. Accordingly, during heating the first portion expands in the first direction while the second portion expands in a second direction to thereby offset expansion provided in the first direction by the first portion. Conversely with cooling of the sample, (e.g., through the introduction of environmental conditioning fluids configured to cool the environmental cavity 206) the first portion of the expansion and contraction linkage moves in the second direction (opposite to the first direction previously described) and the second portion contracts in the first direction opposed to the first direction the first portion moves. Accordingly, with cooling the expansion and contraction linkage 600 cooperates by way of the first and second portions to accordingly maintain the sample elevation and the stage surface elevation substantially static in a similar manner to that provided with heating. That is to say, while the sample 806 (FIG. 8) is maintained at a desired temperature, for instance a steady state temperature approaching 1500 degrees Celsius or less expansion and contraction, thermo-mechanical drift or the like otherwise caused by temperature fluctuations at the sample 806 and within the environmental cavity 206 are accordingly attenuated with the linkage 600. Stated another way, the expansion and contraction linkage 600 cooperates through a combination of opposed expansion or contraction during temperature fluctuations to accordingly maintain the sample and the stage surface 306 at a substantially static elevation.

In another example the method 1000 includes heating or cooling the probe 800 extending through the testing instrument access port. As previously shown in FIG. 9, in one example, the instrument probe 800 positioned within the testing instrument access port 218 is heated with one or more of radiative or convective heating and cooling provided by the environment within the environmental cavity 206. For instance, with the provision of an environmental conditioning fluid (cooled or heated) the fluid provides convective heat transfer to both the sample 300 as well as the probe 800 and accordingly maintains the probe 800 (e.g., the probe tip 804) at a substantially identical temperature to the temperature of the sample on the sample stage 300. In another example, where the environmental cavity 206 is heated for instance by way of the sample heater 304 associated with the sample stage 300 and optionally the top heater 312 the probe tip 804 is heated with radiation based heat transfer. In another example, the probe tip 804 is heated with a combination of radiation and convective heat transfer.

In yet another example, the method 1000 includes throttling heat transfer between the probe tip 804 and an opposed end of the probe shaft for instance a portion of the probe shaft coupled with sensitive instruments, such as a transducer, sensing devices and the like coupled with the opposed end of the probe shaft 802. In one example, throttling heat transfer along the probe 800 for instance away from an opposed end of the probe shaft is accomplished with an environmental conditioning outlet 324 extending into close proximity to the testing instrument access port 218. For instance, as shown in FIG. 9 the environmental conditioning outlet 324 is in communication with the testing instrument access port 218 and accordingly withdraws fluids such as heated or cooled fluids from within the access port to accordingly attenuate heat transfer upwardly along the probe shaft 802. In yet another example, the gas delivery channel 326 also shown in FIG. 9 is used to provide a flow of isolation fluid across the probe 800. The pressurized flow of isolation fluid for, instance an inert gas that is cooled or maintained at room temperature relative to the heated environment within the environmental cavity 206, interrupts the flow of heat along the probe 800. That is to say, the flow of gas provided by the gas delivery channel 326 is transverse to the probe 800 and accordingly interrupts the flow of heated or cooled fluids upwardly along the probe 800 (and provides convective heat transfer for heat within the probe shaft 802) toward sensitive equipment such as transducers.

Optionally the method 1000 further includes conditioning a localized environment around the sample positioned on the sample stage 300 within the environmental cavity 206. As previously described, the environmental cavity 206 has a first volume and an instrument cavity such as the instrument chamber 102 has a second volume, the second volume being larger than the first volume of the environmental cavity 206. By conditioning the localized environment around the sample on the sample stage 300 conditioning of the remainder of the instrument chamber 102 is avoided. Further, interaction of the surrounding environment of the instrument chamber 102 with the sample positioned within the environmental cavity 206 is also avoided.

Optionally, the method 1000 further includes in one example testing of a sample within the environmental conditioning assembly 108. For instance, in one example, a probe such as the probe 800 shown in FIGS. 8 and 9 is introduced through the testing instrument access port 218. The probe 800 conducts one or more mechanical testing procedures including engagement of the probe tip 804 with the sample on the sample stage 300. Engagement of the probe with the sample stage 300 optionally deforms the sample and allows for the measurement of one or more mechanical properties and characteristics of the sample, including but not limited to, the force applied to the sample, the depth of penetration by the probe tip 804 and corresponding mechanical characteristics such as hardness, the modulus of elasticity or the like. In still another example, testing of the sample within the environmental cavity 206 includes electrically biasing a probe tip 804 for instance with the electrical contact 808 shown in FIG. 8. Additionally the sample stage 300 is also biased by the corresponding electrical contact 810. The sample 806 within the environmental cavity 206 is electrically tested by engaging the probe tip 804 with the sample 806 while the sample is positioned on the stage surface 306. One or more electrical characteristics are measured based on this engagement thereby accordingly determining one or more electrical characteristics of the sample 806.

EMBODIMENTS

Embodiment 1 can include an environmental conditioning assembly for use in mechanical testing at scales of microns or less, the environmental conditioning assembly comprising: an enclosure housing including an environmental cavity; a sample stage within the environmental cavity, the sample stage including a stage surface configured to support a sample thereon, and a cavity perimeter of the enclosure housing is clustered around the sample stage; and a sample heating or cooling system configured to heat or cool the sample on the stage surface within the enclosure housing.

Embodiment 2 can include, or can optionally be combined with the subject matter of Embodiment 1, to optionally include wherein the enclosure housing is configured for positioning within an instrument chamber of an instrument assembly, an instrument chamber volume greater than an environmental cavity volume of the environmental cavity.

Embodiment 3 can include, or can optionally be combined with the subject matter of one or any combination of Embodiments 1 or 2 to optionally include wherein the enclosure housing includes a testing instrument access port extending through the enclosure housing into the environmental cavity, an access port perimeter of the testing instrument access port extends around a testing instrument positioned within the testing instrument access port with an actuation gap therebetween.

Embodiment 4 can include, or can optionally be combined with the subject matter of one or any combination of Embodiments 1 through 3 to optionally include wherein the enclosure housing includes a top jacket coupled with a bottom jacket, and the sample stage is interposed between the top and bottom jackets.

Embodiment 5 can include, or can optionally be combined with the subject matter of one or any combination of Embodiments 1-4 to include, wherein the top jacket includes a top heater, and the top jacket and the bottom jacket are configured to clamp a sample between the sample heater of the sample stage and the top heater.

Embodiment 6 can include, or can optionally be combined with the subject matter of Embodiments 1-5 to optionally include, wherein one of the top jacket and the bottom jacket includes one or more guide posts, and the other of the bottom jacket and the top jacket includes one or more linear bearings, and the linear bearings receive the guide posts therein to align the top jacket with the bottom jacket and constrain the top jacket from laterally moving relative to the sample stage.

Embodiment 7 can include, or can optionally be combined with the subject matter of Embodiments 1-6 to optionally include an expansion and contraction linkage including: an interface member having a support interface and a stage interface recessed from the support interface, one or more stage supports coupled with the interface member at the stage interface, the one or more stage supports are coupled with the sample stage, one or more interface supports coupled with the interface member at the support interface, and in either of steady state heated or cooled configurations for a sample the expansion and contraction linkage expands or contracts, respectively, according to temperature fluctuations above and below a steady state temperature, and a stage surface elevation of the stage surface remains substantially static according to expansion and contraction of the expansion and contraction linkage.

Embodiment 8 can include, or can optionally be combined with the subject matter of Embodiments 1-7 to optionally include wherein a bottom jacket of the enclosure housing includes the interface member.

Embodiment 9 can include, or can optionally be combined with the subject matter of Embodiments 1-8 to optionally include wherein: the one or more stage supports and the one or more interface supports expand or contract with the temperature fluctuations in a first direction, and the interface member between the support interface and the stage interface expands and contracts with the temperature fluctuations in a second direction opposed to the first direction, the expansion or contraction of the interface member in the second direction matches the expansion or contraction of the one or more stage supports and the one or more interface supports in the first direction.

Embodiment 10 can include, or can optionally be combined with the subject matter of Embodiments 1-9 to optionally include wherein the one or more stage supports includes at least three support pins positioned around the stage interface, and the at least three support pins are received within corresponding pin recesses of the sample stage.

Embodiment 11 can include, or can optionally be combined with the subject matter of Embodiments 1-10 to optionally include wherein the sample stage includes: a first thickness between the stage surface and an opposed stage surface, and a plurality of pin recesses extending from the opposed stage surface to the stage surface, a recess trough is positioned within each of the plurality of pin recesses, and the recess trough is immediately adjacent to the stage surface, the one or more stage supports include a plurality of support pins with support pin tips received in the plurality of pin recesses and engaged within the recess troughs adjacent to the stage surface, and a second thickness between the stage surface and the recess troughs is less than the first thickness.

Embodiment 12 can include, or can optionally be combined with the subject matter of Embodiments 1-11 to optionally include wherein the one or more interface supports includes three elongated jacket support columns received within support cavities in a bottom jacket of the enclosure housing, each of the jacket support columns includes: an end face engaged with the support interface, and a column body spaced from cavity walls of the respective support cavities of the bottom jacket.

Embodiment 13 can include, or can optionally be combined with the subject matter of Embodiments 1-12 to optionally include wherein the sample heating or cooling system includes a sample heater within the sample stage.

Embodiment 14 can include, or can optionally be combined with the subject matter of Embodiments 1-13 to optionally include wherein the sample heating or cooling system includes: a source of coolant fluid, an environmental conditioning inlet in the enclosure housing, the environmental conditioning inlet in communication with the source of coolant fluid and an environmental cavity of the enclosure housing having the sample stage therein, and an environmental conditioning outlet in the enclosure housing, the environmental conditioning outlet in communication with the environmental cavity.

Embodiment 15 can include, or can optionally be combined with the subject matter of Embodiments 1-14 to optionally include an environmental conditioning assembly for use in mechanical testing at scales of microns or less, the environmental conditioning assembly comprising: an enclosure housing including an environmental cavity therein, the enclosure housing including a top jacket and a bottom jacket surrounding the environmental cavity; a sample stage having a sample surface within the environmental cavity, the sample stage including a sample heater, and the top and bottom jackets are configured to clamp a sample between the sample heater and the top jacket; an expansion and contraction linkage including first and second portions, and each of the first and second portions expand or contract with heating or cooling, respectively, caused by temperature fluctuations, and the expansion or contraction of the first and second portions maintains the sample surface at a static elevation; a testing instrument access port extending through the top jacket into the environmental cavity, and an access port perimeter of the testing instrument access port extends around a testing instrument positioned within the testing instrument access port with an actuation gap therebetween; and wherein the enclosure housing includes a cavity perimeter clustered around the sample stage, and the enclosure housing isolates the environmental cavity and the sample stage from an environment exterior to the enclosure housing.

Embodiment 16 can include, or can optionally be combined with the subject matter of Embodiments 1-15 to optionally include wherein the top jacket is coupled with a top heater, and the top and bottom jackets are configured to clamp a sample between the sample heater and the top heater.

Embodiment 17 can include, or can optionally be combined with the subject matter of Embodiments 1-16 to optionally include wherein the top heater and the sample stage having the sample heater are configured for surface to surface engagement with a sample clamped therebetween.

Embodiment 18 can include, or can optionally be combined with the subject matter of Embodiments 1-17 to optionally include wherein the top heater includes one or more fluid channels, and the one or more fluid channels extend from the environmental cavity to the testing instrument access port.

Embodiment 19 can include, or can optionally be combined with the subject matter of Embodiments 1-18 to optionally include wherein the first portion of the expansion and contraction linkage includes: the bottom jacket, the bottom jacket having a support interface and a stage interface recessed relative to the support interface, and the second portion of the expansion and contraction linkage includes: one or more stage supports coupled with the bottom jacket at the stage interface, and the one or more stage supports are coupled with the sample stage, and one or more jacket supports coupled with the bottom jacket at the support interface.

Embodiment 20 can include, or can optionally be combined with the subject matter of Embodiments 1-19 to optionally include wherein: the first portion of the expansion and contraction linkage expands or contracts with temperature fluctuations in a first direction, and the second portion of the expansion and contraction linkage expands or contracts with temperature fluctuations in a second direction opposed to the first direction, the expansion or contraction of the second portion in the second direction matches the expansion or contraction of the first portion in the first direction.

Embodiment 21 can include, or can optionally be combined with the subject matter of Embodiments 1-20 to optionally include wherein a jacket seal is coupled with one of the top and bottom jackets, and the jacket seal is engaged with the other of the bottom and top jackets to seal an interface between the top and bottom jackets.

Embodiment 22 can include, or can optionally be combined with the subject matter of Embodiments 1-21 to optionally include wherein the enclosure housing includes an environmental conditioning fluid inlet extending into the environmental cavity, and the envelope housing includes an environmental conditioning fluid outlet extending out of the environmental cavity.

Embodiment 23 can include, or can optionally be combined with the subject matter of Embodiments 1-22 to optionally include wherein the environmental conditioning fluid outlet includes a vacuum port near the testing instrument access port, and the vacuum port withdraws heated environmental conditioning fluid on or before the heated environmental conditioning fluid leaves the testing instrument access port.

Embodiment 24 can include, or can optionally be combined with the subject matter of Embodiments 1-23 to optionally include wherein the enclosure housing includes one or more heating or coolant passages extending through the enclosure housing.

Embodiment 25 can include, or can optionally be combined with the subject matter of Embodiments 1-24 to optionally include wherein an insulation ring fills a portion of the environmental cavity between the sample stage and the cavity perimeter of the enclosure housing.

Embodiment 26 can include, or can optionally be combined with the subject matter of Embodiments 1-25 to optionally include a method for using an environmental conditioning assembly comprising: positioning a sample on a sample surface of a sample stage within an environmental cavity of an enclosure housing, a cavity perimeter of the enclosure housing is clustered around the sample stage and the sample; heating or cooling the sample in the environmental cavity at a steady state temperature with a sample heating or cooling system, heating or cooling at the steady temperature including temperature fluctuations above and below the steady state temperature; during heating or cooling maintaining a sample elevation and a stage surface elevation substantially static with the temperature fluctuations through expansion and contraction of an expansion and contraction linkage coupled between the enclosure housing and the sample stage; and accessing the sample through a testing instrument access port with a probe, the testing instrument access port extends through the enclosure housing into the environmental cavity, and an access port perimeter of the testing instrument access port extends around a testing instrument positioned within the testing instrument access port with an actuation gap therebetween.

Embodiment 27 can include, or can optionally be combined with the subject matter of Embodiments 1-26 to optionally include clamping the sample between a top jacket and bottom jacket of the enclosure housing.

Embodiment 28 can include, or can optionally be combined with the subject matter of Embodiments 1-27 to optionally include wherein clamping the sample includes engaging the sample stage against a first surface of the sample and engaging a top heater coupled with the top jacket with a second surface of the sample.

Embodiment 29 can include, or can optionally be combined with the subject matter of Embodiments 1-28 to optionally include wherein heating the sample includes heating with the sample heater and the top heater at both of the first and second surfaces of the sample.

Embodiment 30 can include, or can optionally be combined with the subject matter of Embodiments 1-29 to optionally include wherein heating the sample includes: heating the sample at the first surface to a first temperature with the sample heater, and heating the sample at the second surface to a second temperature with the top heater, the second temperature different from the first temperature.

Embodiment 31 can include, or can optionally be combined with the subject matter of Embodiments 1-30 to optionally include aligning the top jacket with the bottom jacket before clamping of the sample, and constraining lateral movement of the top jacket or a component coupled with the top jacket and engaged with the sample during clamping of the sample.

Embodiment 32 can include, or can optionally be combined with the subject matter of Embodiments 1-31 to optionally include wherein maintaining the sample elevation and the stage surface elevation substantially static during heating of the sample includes expanding a first portion of the expansion and contraction linkage in a first direction and expanding a second portion of the expansion and contraction linkage in a second direction opposed to the first direction.

Embodiment 33 can include, or can optionally be combined with the subject matter of Embodiments 1-32 to optionally include expanding the first portion of the expansion and contraction linkage includes expanding one or more interface supports coupled with an interface member and expanding one or more stage supports coupled between the interface member and the sample stage in the first direction, and expanding the second portion of the expansion and contraction linkage includes expanding the interface member between the one or more interface supports and the one or more stage supports in the second direction.

Embodiment 34 can include, or can optionally be combined with the subject matter of Embodiments 1-33 to optionally include wherein maintaining the sample elevation and the stage surface elevation substantially static during cooling of the sample includes contracting a first portion of the expansion and contraction linkage in a first direction and contracting a second portion of the expansion and contraction linkage in a second direction opposed to the first direction.

Embodiment 35 can include, or can optionally be combined with the subject matter of Embodiments 1-34 to optionally include wherein: contracting the first portion of the expansion and contraction linkage includes contracting one or more interface supports coupled with an interface member and contracting one or more jacket supports coupled between the interface member and the sample stage in the first direction, and contracting the second portion of the expansion and contraction linkage includes contracting the interface member between the one or more interface supports and the one or more stage supports in the second direction.

Embodiment 36 can include, or can optionally be combined with the subject matter of Embodiments 1-35 to optionally include heating or cooling the probe extending through the testing instrument access port.

Embodiment 37 can include, or can optionally be combined with the subject matter of Embodiments 1-36 to optionally include wherein heating or cooling the probe includes heating or cooling one or more of an end of a probe shaft and a probe tip coupled at the end to a temperature substantially the same as the steady state temperature of the sample through the heating or cooling in the environmental cavity, and further comprising throttling heat transfer between the probe tip and the and an opposed end of the probe shaft.

Embodiment 38 can include, or can optionally be combined with the subject matter of Embodiments 1-37 to optionally include observing the sample through an access port cone of the testing instrument access port.

Embodiment 39 can include, or can optionally be combined with the subject matter of Embodiments 1-38 to optionally include conditioning a localized environment around and at the sample within the environmental cavity, wherein the environmental cavity has a first volume, and an instrument cavity having a second volume contains the enclosure housing therein, the second volume larger than the first volume.

Embodiment 40 can include, or can optionally be combined with the subject matter of Embodiments 1-39 to optionally include wherein conditioning the localized environment includes one or more of: heating one or more of the sample or the localized environment, cooling one or more of the sample or the localized environment, introducing a conditioning fluid to the environmental cavity including one or more of inert gases, air, reactive fluids or liquids, and controlling the humidity of the environmental cavity.

Embodiment 41 can include, or can optionally be combined with the subject matter of Embodiments 1-40 to optionally include conditioning the localized environment includes introducing a conditioning fluid at an environmental conditioning inlet in the enclosure housing and withdrawing the conditioning fluid at an environmental conditioning outlet.

Embodiment 42 can include, or can optionally be combined with the subject matter of Embodiments 1-41 to optionally include withdrawing a heated or cooled fluid from the environmental cavity at an environmental conditioning outlet adjacent to the testing instrument access port, and isolating a probe transducer from the heated or cooled fluid according to withdrawing of the heated or cooled fluid with the environmental conditioning outlet.

Embodiment 43 can include, or can optionally be combined with the subject matter of Embodiments 1-42 to optionally include mechanically testing the heated or cooled sample within the environmental cavity with the probe extending through the instrument access port.

Embodiment 44 can include, or can optionally be combined with the subject matter of Embodiments 1-43 to optionally include electrically biasing a probe tip and the sample stage, and electrically testing the heated or cooled sample within the environmental cavity with the probe extending through the instrument access port according to a measured electrical characteristic.

Each of these non-limiting Embodiments can stand on its own, or can be combined in any permutation or combination with any one or more of the other Embodiments.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be com- The claimed invention is:

1. An environmental conditioning assembly for use in mechanical testing at scales of microns or less, the environmental conditioning assembly comprising:
   an enclosure housing including an environmental cavity, and the enclosure housing includes:
      a top jacket coupled with a bottom jacket, the top jacket includes a heater,
      a testing instrument access port extending through the enclosure housing into the environmental cavity, and
      an access port perimeter of the testing instrument access port extends around a testing instrument positionable within the testing instrument access port with an actuation gap therebetween, the actuation gap spacing the access port perimeter from the testing instrument;
   a sample stage within the environmental cavity and interposed between the top and bottom jackets, the sample stage including a stage surface configured to support a sample thereon, and a cavity perimeter of the enclosure housing is clustered around the sample stage;
   a sample heating or cooling system configured to heat or cool the sample on the stage surface within the enclosure housing, the sample heating or cooling system includes a sample heater coupled with the sample stage; and
   wherein the top and bottom jackets are configured to clamp the sample therebetween and couple the top heater and the sample heater with the sample.

2. The environmental conditioning assembly of claim 1, wherein the enclosure housing is configured for positioning within an instrument chamber of an instrument assembly, an instrument chamber volume greater than an environmental cavity volume of the environmental cavity.

3. The environmental conditioning assembly of claim 1 comprising an expansion and contraction linkage including:
   an interface member having a support interface and a stage interface recessed from the support interface, one or more stage supports coupled with the interface member at the stage interface, the one or more stage supports are coupled with the sample stage, one or more interface supports coupled with the interface member at the support interface, and in either of steady state heated or cooled configurations for a sample the expansion and contraction linkage expands or contracts, respectively, according to temperature fluctuations above and below a steady state temperature, and a stage surface elevation of the stage surface remains substantially static according to expansion and contraction of the expansion and contraction linkage.

4. The environmental conditioning assembly of claim 3, wherein:
   the one or more stage supports and the one or more interface supports expand or contract with the temperature fluctuations in a first direction, and the interface member between the support interface and the stage interface expands and contracts with the temperature fluctuations in a second direction opposed to the first direction, the expansion or contraction of the interface member in the second direction matches the expansion or contraction of the one or more stage supports and the one or more interface supports in the first direction.

5. The environmental conditioning assembly of claim 3, wherein the sample stage includes:
   a first thickness between the stage surface and an opposed stage surface, and a plurality of pin recesses extending from the opposed stage surface to the stage surface, a recess trough is positioned within each of the plurality of pin recesses, and the recess trough is immediately adjacent to the stage surface, the one or more stage supports include a plurality of support pins with support pin tips received in the plurality of pin recesses and engaged within the recess troughs adjacent to the stage surface, and a second thickness between the stage surface and the recess troughs is less than the first thickness.

6. The environmental conditioning assembly of claim 1, wherein the sample heating or cooling system includes a sample heater within the sample stage.

7. The environmental conditioning assembly of claim 1, wherein the sample heating or cooling system includes:
   a source of coolant fluid, an environmental conditioning inlet in the enclosure housing, the environmental conditioning inlet in communication with the source of coolant fluid and an environmental cavity of the enclosure housing having the sample stage therein, and an environmental conditioning outlet in the enclosure housing, the environmental conditioning ou e in communication with the environmental cavity.

8. The environmental conditioning assembly of claim 1, wherein the enclosure housing includes an environmental conditioning fluid inlet extending into the environmental cavity, and the envelope housing includes an environmental conditioning fluid outlet extending out of the environmental cavity.

9. The environmental conditioning assembly of claim 8, wherein the environmental conditioning fluid outlet includes a vacuum port near the testing instrument access port, and the vacuum port withdraws heated environmental conditioning fluid on or before the heated environmental conditioning fluid leaves the testing instrument access port.

10. The environmental conditioning assembly of claim 1, wherein the top and bottom jackets are configured to engage the top heater and the sample heater with the sample.

11. An environmental conditioning assembly for use in mechanical testing at scales of microns or less, the environmental conditioning assembly comprising:
   an enclosure housing including an environmental cavity therein, the enclosure housing including a top jacket and a bottom jacket surrounding the environmental cavity;
   a sample stage having a sample surface within the environmental cavity, the sample stage including a sample heater, and the top and bottom jackets are configured to clamp a sample between the sample heater and the top jacket;
   an expansion and contraction linkage including first and second portions, and each of the first and second portions expand or contract with heating or cooling, respectively, caused by temperature fluctuations, and the expansion or contraction of the first and second portions maintains the sample surface at a static elevation;
   a testing instrument access port extending through the top jacket into the environmental cavity, and an access port perimeter of the testing instrument access port extends around a testing instrument positioned within the testing instrument access port with an actuation gap therebetween; and wherein the enclosure housing includes a cavity perimeter clustered around the sample stage, and the enclosure housing isolates the environmental cavity and the sample stage from an environment exterior to the enclosure housing.

12. The environmental conditioning assembly of claim 11, wherein the top jacket is coupled with atop heater, and the top and bottom jackets are configured to clamp a sample between the sample heater and the top heater.

13. The environmental conditioning assembly of claim 12, wherein the top heater and the sample stage having the sample heater are configured for surface to surface engagement with a sample clamped therebetween.

14. The environmental conditioning assembly of claim 12, wherein the first portion of the expansion and contraction linkage includes:
the bottom jacket, the bottom jacket having a support interface and a stage interface recessed relative to the support interface, and
the second portion of the expansion and contraction linkage includes:
one or more stage supports coupled with the bottom jacket at the stage interface, and the one or more stage supports are coupled with the sample stage, and one or more jacket supports coupled with the bottom jacket at the support interface.

15. The environmental conditioning assembly of claim 11, wherein:
the first portion of the expansion and contraction linkage expands or contracts with temperature fluctuations in a first direction, and the second portion of the expansion and contraction linkage expands or contracts with temperature fluctuations in a second direction opposed to the first direction, the expansion or contraction of the second portion in the second direction matches the expansion or contraction of the first portion in the first direction.

16. The environmental conditioning assembly of claim 11, wherein a jacket seal is coupled with one of the top and bottom jackets, and the jacket seal is engaged with the other of the bottom and top jackets to seal an interface between the top and bottom jackets.

17. The environmental conditioning assembly of claim 11, wherein the enclosure housing includes an environmental conditioning fluid inlet extending into the environmental cavity, and the envelope housing includes an environmental conditioning fluid outlet extending out of the environmental cavity.

18. The environmental conditioning assembly of claim 17, wherein the environmental conditioning fluid outlet includes a vacuum port near the testing instrument access port, and the vacuum port withdraws heated environmental conditioning fluid on or before the heated environmental conditioning fluid leaves the testing instrument access port.

19. A method for using an environmental conditioning assembly comprising:
positioning a sample on a sample surface of a sample stage within an environmental cavity of an enclosure housing, a cavity perimeter of the enclosure housing is clustered around the sample stage and the sample;
heating or cooling the sample in the environmental cavity at a steady state temperature with a sample heating or cooling system, heating or cooling at the steady temperature including temperature fluctuations above and below the steady state temperature;
during heating or cooling maintaining a sample elevation and a stage surface elevation substantially static with the temperature fluctuations through expansion and contraction of an expansion and contraction linkage coupled between the enclosure housing and the sample stage; and
accessing the sample through a testing instrument access port with a probe, the testing instrument access port extends through the enclosure housing into the environmental cavity, and an access port perimeter of the testing instrument access port extends around a testing instrument positioned within the testing instrument access port with an actuation gap therebetween.

20. The method of claim 19 comprising clamping the sample between a top jacket and bottom jacket of the enclosure housing.

21. The method of claim 20, wherein clamping the sample includes engaging the sample stage against a first surface of the sample and engaging a top heater coupled with the top jacket with a second surface of the sample.

22. The method of claim 21, wherein heating the sample includes heating with the sample heater and the top heater at both of the first and second surfaces of the sample.

23. The method of claim 19, wherein maintaining the sample elevation and the stage surface elevation substantially static during heating of the sample includes expanding a first portion of the expansion and contraction linkage in a first direction and expanding a second portion of the expansion and contraction linkage in a second direction opposed to the first direction.

24. The method of claim 19, wherein maintaining the sample elevation and the stage surface elevation substantially static during cooling of the sample includes contracting a first portion of the expansion and contraction linkage in a first direction and contracting a second portion of the expansion and contraction linkage in a second direction opposed to the first direction.

25. The method of claim 19 comprising:
heating or cooling the probe extending through the testing instrument access port, heating or cooling the probe includes heating or cooling one or more of an end of a probe shaft and a probe tip coupled at the end to a temperature substantially the same as the steady state temperature of the sample through the heating or cooling in the environmental cavity, and further comprising throttling heat transfer between the probe tip and the and an opposed end of the probe shaft.

26. The method of claim 19 comprising conditioning a localized environment around and at the sample within the environmental cavity, wherein the environmental cavity has a first volume, and an instrument cavity having a second volume contains the enclosure housing therein, the second volume larger than the first volume.

27. The method of claim 26, wherein conditioning the localized environment includes one or more of:
heating one or more of the sample or the localized environment, cooling one or more of the sample or the localized environment, introducing a conditioning fluid to the environmental cavity including one or more of inert gases, air, reactive fluids or liquids, and controlling the humidity of the environmental cavity.

28. The method of claim 19 comprising:
withdrawing a heated or cooled fluid from the environmental cavity at an environmental conditioning outlet adjacent to the testing instrument access port, and isolating a probe transducer from the heated or cooled fluid according to withdrawing of the heated or cooled fluid with the environmental conditioning outlet.

29. The method of claim 19 comprising:
electrically biasing a probe tip and the sample stage, and electrically testing the heated or cooled sample within the environmental cavity with the probe extending through the instrument access port according to a measured electrical characteristic.

\* \* \* \* \*

UNITED STATES PATENT AND TRADEMARK OFFICE
CERTIFICATE OF CORRECTION

PATENT NO. : 9,829,417 B2
APPLICATION NO. : 14/407783
DATED : November 28, 2017
INVENTOR(S) : Schmitz et al.

Page 1 of 1

It is certified that error appears in the above-identified patent and that said Letters Patent is hereby corrected as shown below:

On the Title Page

On page 4, in Column 1, under "Other Publications", Line 52, delete "15, 2015"," and insert --15, 2016",-- therefor In the Claims In Column 31, Line 13, in Claim 1, after "a", insert --top--

In Column 32, Line 26, in Claim 7, delete "ou e" and insert --outlet-- therefor

In Column 33, Line 7, in Claim 12, delete "atop" and insert --a top-- therefor

Signed and Sealed this
Eleventh Day of June, 2019

Andrei Iancu
*Director of the United States Patent and Trademark Office*